(12) United States Patent
Mernoe et al.

(10) Patent No.: US 9,814,830 B2
(45) Date of Patent: *Nov. 14, 2017

(54) DISPENSING FLUID FROM AN INFUSION PUMP SYSTEM

(71) Applicant: Bigfoot Biomedical, Inc., Milpitas, CA (US)

(72) Inventors: Morten Mernoe, Copenhagen O (DK); Mitchell Wenger, Ross, CA (US); James Causey, Simi Valley, CA (US); Todd Kirschen, Palo Alto, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 686 days.

This patent is subject to a terminal disclaimer.

(21) Appl. No.: 13/936,684

(22) Filed: Jul. 8, 2013

(65) Prior Publication Data

US 2013/0296789 A1    Nov. 7, 2013

Related U.S. Application Data

(60) Continuation of application No. 13/616,303, filed on Sep. 14, 2012, now Pat. No. 8,480,623, which is a
(Continued)

(51) Int. Cl.
*A61M 5/145* (2006.01)
*A61M 5/315* (2006.01)
*A61M 5/142* (2006.01)

(52) U.S. Cl.
CPC ...... *A61M 5/1454* (2013.01); *A61M 5/14244* (2013.01); *A61M 5/14566* (2013.01);
(Continued)

(58) Field of Classification Search
CPC .... A61M 5/14566; A61M 2005/14506; A61M 5/1454; A61M 2005/31518
See application file for complete search history.

(56) References Cited

U.S. PATENT DOCUMENTS 2,605,765 A    8/1952  Kollsman
3,688,764 A    9/1972  Reed
(Continued)

FOREIGN PATENT DOCUMENTS

CA    2543545        5/2005
DE    196 27 619 A   1/1998
(Continued)

OTHER PUBLICATIONS

International Search Report and Written Opinion in International Application No. PCT/US2006/036368, dated Mar. 27, 2007, 14 pages.
(Continued)

*Primary Examiner* — Theodore Stigell
*Assistant Examiner* — Benjamin Koo
(74) *Attorney, Agent, or Firm* — Fish & Richardson P.C.

(57) ABSTRACT

Some embodiments of an infusion pump device may include a drive system that accurately and incrementally dispenses fluid from the pump device in a controlled manner. Particular embodiments of the drive system may include a rotational motor that is coupled to a string member, which is used to adjust a pawl relative to a ratchet body. In such circumstances, the drive system can provide a reliable and compact infusion pump device that accurately dispenses the desired volume of fluid.

9 Claims, 14 Drawing Sheets

Related U.S. Application Data division of application No. 13/070,569, filed on Mar. 24, 2011, now Pat. No. 8,282,601, which is a continuation of application No. 12/422,711, filed on Apr. 13, 2009, now Pat. No. 7,938,803, which is a division of application No. 11/522,560, filed on Sep. 18, 2006, now Pat. No. 7,534,226.

(60) Provisional application No. 60/720,411, filed on Sep. 26, 2005, provisional application No. 60/720,405, filed on Sep. 26, 2005, provisional application No. 60/721,267, filed on Sep. 28, 2005.

(52) U.S. Cl.
CPC ............ *A61M 2005/14506* (2013.01); *A61M 2005/31518* (2013.01); *A61M 2205/8212* (2013.01)

(56) References Cited

U.S. PATENT DOCUMENTS

| | | |
|---|---|---|
| 3,886,938 A | 6/1975 | Szabo et al. |
| 4,077,405 A | 3/1978 | Haerten et al. |
| 4,231,368 A | 11/1980 | Becker |
| 4,235,234 A | 11/1980 | Whitney et al. |
| 4,265,241 A | 5/1981 | Portner et al. |
| 4,300,554 A | 11/1981 | Hessberg et al. |
| 4,313,439 A | 2/1982 | Babb et al. |
| 4,360,019 A | 11/1982 | Portner et al. |
| 4,373,527 A | 2/1983 | Fischell |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,562,751 A | 1/1986 | Nason et al. |
| 4,619,653 A | 10/1986 | Fischell |
| 4,652,260 A | 3/1987 | Fenton et al. |
| 4,668,220 A | 5/1987 | Hawrylenko |
| 4,678,408 A | 7/1987 | Nason et al. |
| 4,734,092 A | 3/1988 | Millerd |
| 4,850,817 A | 7/1989 | Nason et al. |
| 4,902,278 A | 2/1990 | Maget et al. |
| 5,045,064 A | 9/1991 | Idriss |
| 5,088,981 A | 2/1992 | Howson et al. |
| 5,176,632 A | 1/1993 | Bernardi |
| 5,190,522 A | 3/1993 | Wojcicki et al. |
| 5,209,230 A | 5/1993 | Swedlow et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,429,602 A | 7/1995 | Hauser |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,656,032 A | 8/1997 | Kriesel et al. |
| 5,665,065 A | 9/1997 | Colman et al. |
| 5,672,167 A | 9/1997 | Athayde et al. |
| 5,693,018 A | 12/1997 | Kriesel et al. |
| 5,718,562 A | 2/1998 | Lawless |
| 5,741,216 A | 4/1998 | Hemmingsen et al. |
| 5,764,034 A | 6/1998 | Bowman et al. |
| 5,772,635 A | 6/1998 | Dastur et al. |
| 5,800,420 A | 9/1998 | Grose et al. |
| 5,816,306 A | 10/1998 | Giacomel |
| 5,851,197 A | 12/1998 | Marano et al. |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,127,061 A | 10/2000 | Shun et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,491,684 B1 | 12/2002 | Joshi et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,537,268 B1 | 3/2003 | Gibson et al. |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,668 B1 | 12/2003 | Kleeman et al. |
| 6,669,669 B2 | 12/2003 | Flaherty et al. |
| 6,685,674 B2 | 2/2004 | Douglad et al. |
| 6,687,546 B2 | 2/2004 | Lebel et al. |
| 6,689,100 B2 | 2/2004 | Connelly et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |

(56) References Cited

U.S. PATENT DOCUMENTS

| | | |
|---|---|---|
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,070,580 B2 | 7/2006 | Nielsen |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,172,572 B2 | 2/2007 | Diamond et al. |
| 7,232,423 B2 | 6/2007 | Mernoe |
| 7,494,481 B2 | 2/2009 | Moberg et al. |
| 7,641,649 B2 | 1/2010 | Moberg et al. |
| 2001/0041869 A1 | 11/2001 | Causey, III et al. |
| 2001/0056262 A1 | 12/2001 | Cabiri |
| 2002/0004651 A1 | 1/2002 | Ljunggreen et al. |
| 2002/0007154 A1 | 1/2002 | Hansen et al. |
| 2002/0016568 A1 | 2/2002 | Lebel |
| 2002/0032402 A1 | 3/2002 | Daoud et al. |
| 2002/0040208 A1 | 4/2002 | Flaherty et al. |
| 2002/0072720 A1 | 6/2002 | Hague et al. |
| 2002/0091358 A1 | 7/2002 | Klitmose |
| 2002/0126036 A1 | 9/2002 | Flaherty et al. |
| 2002/0156462 A1 | 10/2002 | Stultz |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0161744 A1 | 8/2003 | Vilks et al. |
| 2003/0198558 A1 | 10/2003 | Nason et al. |
| 2003/0199825 A1 | 10/2003 | Flaherty |
| 2003/0216683 A1 | 11/2003 | Shekalim |
| 2003/0216686 A1 | 11/2003 | Lynch et al. |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0115068 A1 | 6/2004 | Hansen et al. |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0158207 A1 | 8/2004 | Hunn et al. |
| 2004/0171983 A1 | 9/2004 | Sparks et al. |
| 2004/0176727 A1 | 9/2004 | Shekalim |
| 2004/0187952 A1 | 9/2004 | Jones |
| 2004/0204673 A1 | 10/2004 | Flaherty |
| 2004/0204744 A1 | 10/2004 | Penner et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0101933 A1 | 5/2005 | Marrs et al. |
| 2005/0113745 A1 | 5/2005 | Stultz |
| 2005/0124866 A1 | 6/2005 | Elaz et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0088271 A1 | 4/2007 | Richards |
| 2007/0093750 A1 | 4/2007 | Jan et al. |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0009824 A1 | 1/2008 | Moberg et al. |
| 2008/0208627 A1 | 8/2008 | Skyggebjerg |

FOREIGN PATENT DOCUMENTS

| | | |
|---|---|---|
| DE | 102 36 669 | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |

(56) References Cited

FOREIGN PATENT DOCUMENTS

| | | |
|---|---|---|
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Accu-Chek Spirit, "Pump Therapy Made for You," Roche, 2006, 6 pages.
Collins and Lee, "Microfluidic flow transducer based on the measurement of electrical admittance," *Lab Chip*, 2004, 4:7-10.
Debiotech News Release, "Debiotech reveals its new miniaturized Disposable Insulin Nanopump™ for Diabetes therapy," available at http://www.debiotech.com/news/nw_159.html Apr. 24, 2006, 3 pages.
Medtronic News Release, "Medtronic Receives FDA Approval for World's First Insulin Pump with Real-time Continuous Glucose Monitoring," Apr. 13, 2006, 3 pages.
OmniPod Insulin Management System-Investor Relations-Press Release, Feb. 1, 2005, http://investors.insulet.com/phoenix.zhtml?c=209336&p=irol-newsArticle&ID=988708&highlight= 1 page.
OmniPod Quick Start Guide, 2007, 2 pages.
Patent Abstracts of Japan, vol. 1999, No. 04, and JP 11 010036 , Apr. 30, 1999 and Jan. 19, 1999, Toray Ind. Inc.
The Medtronic Diabetes Connection, 2006, 6 pages.
Xilas Temp Touch, "The latest in high-tech and convenient devices," DOCNews, vol. 2, No. 7, Jul. 1, 2005, http://docnews.diabetesjournals,ord/egi/content/full/2/7/13, 3 pages.

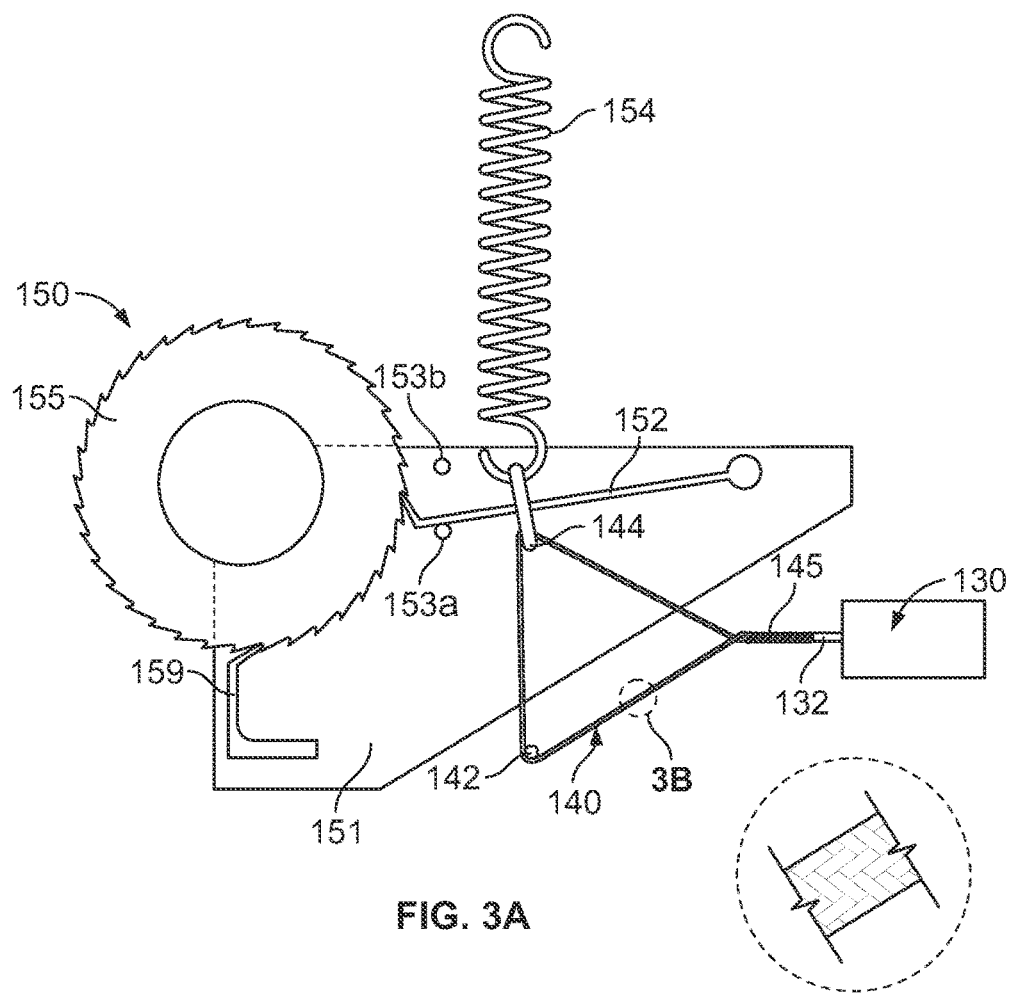
FIG. 3A
FIG. 3B
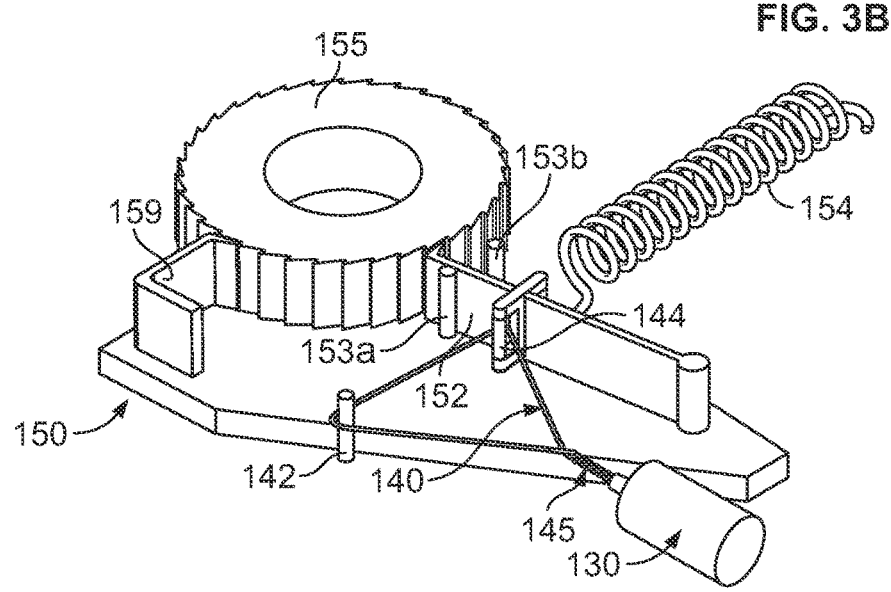
FIG. 3C

DISPENSING FLUID FROM AN INFUSION PUMP SYSTEM

CROSS-REFERENCE TO RELATED APPLICATIONS

This application is a continuation of U.S. application Ser. No. 13/616,303, filed on Sep. 14, 2012 (now U.S. Pat. No. 8,480,623), which is a divisional of U.S. application Ser. No. 13/070,569, filed on Mar. 24, 2011 (now U.S. Pat. No. 8,282,601), which is a continuation application of U.S. application Ser. No. 12/422,711, filed on Apr. 13, 2009 (now U.S. Pat. No. 7,938,803), which is a divisional application of U.S. application Ser. No. 11/522,560, filed on Sep. 18, 2006 (now U.S. Pat. No. 7,534,226), which claims priority to (1) U.S. Provisional Application Ser. No. 60/720,411 filed on Sep. 26, 2005 by Mernoe et al. and entitled "Precision Drive Mechanism," (2) U.S. Provisional Application Ser. No. 60/720,405 filed on Sep. 26, 2005 by Mernoe et al. and entitled "Flexible Pushrod Mechanism," and (3) U.S. Provisional Application Ser. No. 60/721,267 filed on Sep. 28, 2005 by Estes et al. and entitled "Infusion Pump with Removable Controller." The entire contents of these prior applications are fully incorporated by reference herein.

TECHNICAL FIELD

This document relates to an infusion pump system, such as a medical infusion pump system.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

A number of factors may affect the design of infusion pump devices. One such factor is the size of the device. The device may be sized to house the various pump components, yet a large device may reduce the portability for the user. Another factor that may affect the design of an infusion pump device is the convenience to the user. For example, if the device is designed to be a reusable dispenser having high-cost components, it may be expensive and inconvenient for the user to replace such a device that has been lost or damaged. A number of infusion pump components can impact the overall size of the device and the convenience to the user.

SUMMARY

Some embodiments of an infusion pump device may include a drive system that accurately and incrementally dispenses fluid from the pump device in a controlled manner. Particular embodiments of the drive system may include a rotational motor that is coupled to a string member, which is used to adjust a pawl member relative to a ratchet body. This operation of the drive system may cause incremental longitudinal advancement of a piston rod in the infusion pump device, which forces a controlled amount of fluid from the pump device. In such circumstances, the drive system can be part of a reliable and compact infusion pump device that accurately dispenses the desired volume of fluid.

In some embodiments, a medical infusion pump system may include a pump device having a drive system to cause dispensation of a medicine. The drive system may include a pawl that is adjustable relative to a ratchet body. The pawl may engage one or more teeth of the ratchet body to incrementally advance the ratchet body. The drive system may also include a string member coupled to the pawl. The string member may be arranged in a loop around two or more guide structures. The drive system may further include a rotational motor coupled to the string member so that rotation by the motor causes the string member to adjust the pawl relative to the ratchet body. In certain aspects, the medical infusion pump system may include a removable controller device that is mechanically and electrically connectable to the pump device.

Particular embodiments of a medical infusion pump system may include a pump device having a drive system to cause dispensation of a medicine. The drive system may include a pawl that is adjustable relative to a ratchet body. The pawl may engage one or more teeth of the ratchet body to incrementally advance the ratchet body. The drive system may also include a flexible member coupled to the pawl and a spindle coupled to the flexible member. The drive system may further include a rotational motor coupled to the spindle so that rotation by the motor causes the flexible member to wind or unwind around spindle to thereby adjust the pawl relative to the ratchet body.

Some embodiments of a medical infusion pump system may include a pump device and a controller device that is electrically connectable to the pump device to control operation of the drive system. The pump device may include a housing that defines a cavity to receive a medicine and a drive system to cause dispensation of the medicine when the medicine is received in the cavity. The drive system may include a rotational motor and a string member coupled to the motor. The string member may comprise braided filaments.

In certain embodiments, a method for dispensing medicine from an infusion pump system includes rotating a motor one or more full rotations in a first rotational direction to unwind a string member from a spindle and thereby adjust a ratchet mechanism coupled to a piston rod. The adjustment of the ratchet mechanism may incrementally advance the piston rod in a forward direction to force medicine from a wearable medicine dispenser device. The method may also include continuing to rotate the motor in the first rotational direction so that the string member winds around the spindle and thereby applies a tension force to reset the ratchet mechanism. The method may include, in a next dispensing cycle, rotating the motor one or more full rotations in an opposite, second rotational direction to unwind the string member from the spindle and thereby adjust the ratchet mechanism coupled to the piston rod. The adjustment of the ratchet mechanism may incrementally advance the piston rod in the forward direction to force medicine from the wearable medicine dispenser device.

Some embodiments of a method for dispensing medicine from an infusion pump system may include rotating a motor to unwind a string member from a spindle and thereby adjust a ratchet mechanism coupled to a piston rod. The adjustment of the ratchet mechanism may incrementally advance the piston rod in a forward direction to force medicine from a wearable medicine dispenser device. The method may also include rotating the motor to wind the string member around the spindle and thereby apply a tension force to reset the ratchet mechanism.

These and other embodiments may provide one or more of the following advantages. First, the drive system of the pump device can provide a reliable and consistent configuration for accurately dispensing the desired volume of fluid from the pump device. Second, some embodiments of the drive system may comprise few, if any, high-cost components, thereby facilitating the production of a disposable infusion pump device. Third, the pump device may house the drive system in a compact manner so that the pump device is portable, wearable, and readily concealable by the user. As such, a user can conveniently wear the pump device on the user's skin underneath clothing or carry the pump device in the user's pocket (or other portable location) while receiving the medicine dispensed from the pump device. Fifth, in some embodiments, a string member of the drive system can be arranged in a loop around two or more guides so as to optimize the location and direction of the force applied by the string member and to provide a force amplification effect. Sixth, the string member of the driver system may comprise braided filaments that are capable of enduring the torsion and frictional forces associated with undergoing a multitude of motion cycles. Seventh, some embodiments of the infusion pump system may include a removable controller device having a user interface. Such a configuration may provide the user with the ability to monitor the device settings by simply viewing the pump device (e.g., no need for a separate device for reviewing the pump settings). Moreover, the removable controller configuration may provide the user with the ability to dispose of the pump body while reusing the removable controller with a new, subsequent pump body (e.g., maintaining the previous user settings while receiving a new supply of medicine). Eighth, the pump device can be configured to receive a preloaded medicine cartridge (e.g., preloaded with insulin or another medicine for use in the treatment of Diabetes) so as to facilitate low manufacturing costs and high speed assembly.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A is a diagram of a portion of the pump device of FIG. 1.

FIG. 3B is a magnified view of a string member of FIG. 3A.

FIG. 3C is a perspective view of the portion of the pump device of FIG. 3A.

Like reference symbols in the various drawings indicate like elements.

DETAILED DESCRIPTION OF ILLUSTRATIVE EMBODIMENTS

Figure 1:
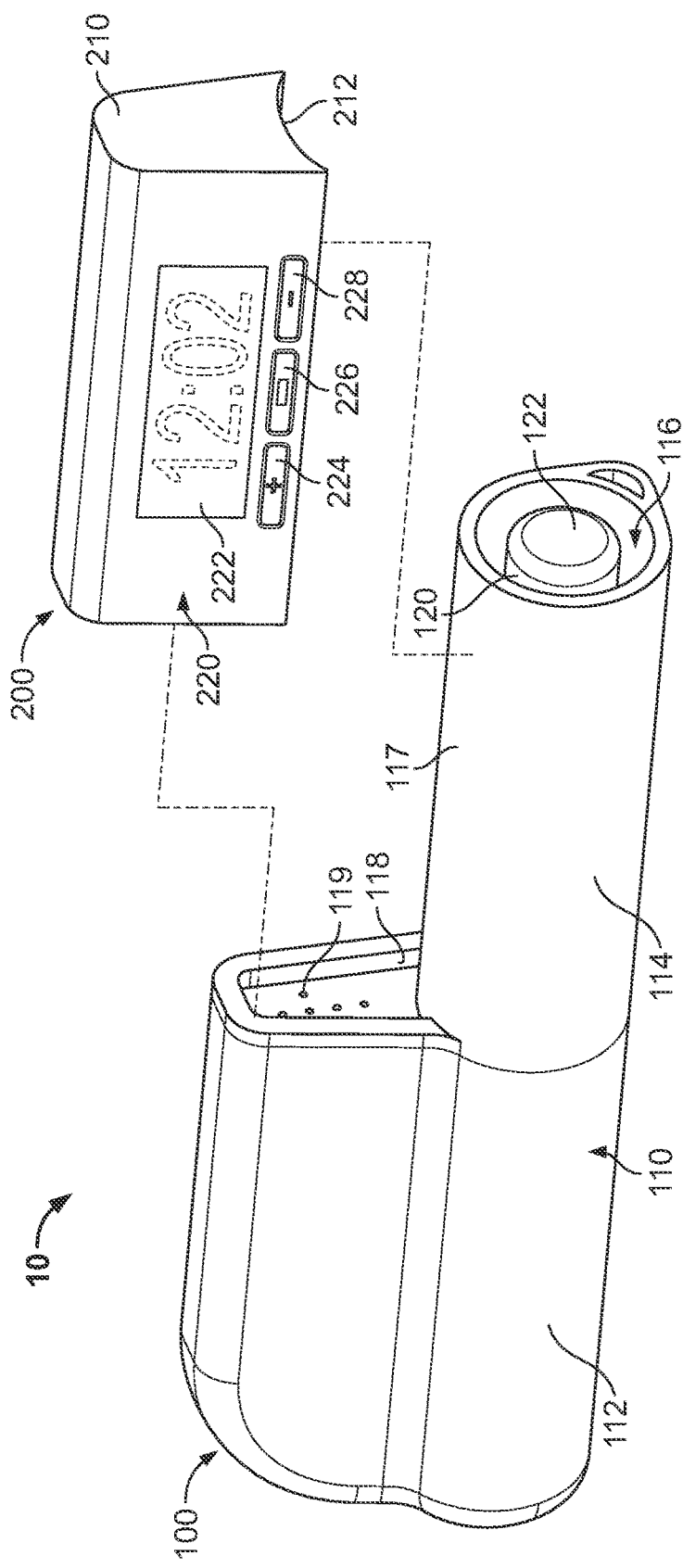
FIG. 1 is a perspective view of an infusion pump system, in accordance with some embodiments.

Referring to FIG. 1, some embodiments of an infusion pump system 10 include a pump device 100 that can communicate with a controller device 200. The pump device 100 includes a housing structure 110 that defines a cavity 116 in which a fluid cartridge 120 is received. In this embodiment, the pump system 10 in a medical infusion pump system that is configured to controllably dispense a medicine from the cartridge 120. As such, the fluid cartridge 120 may contain a medicine to be infused into the tissue or vasculature of a targeted individual, such as a human or animal patient. For example, the pump device 100 can be adapted to receive a medicine cartridge 120 in the form of carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines.

As described in more detail below, the pump device 100 includes a drive system that causes controlled dispensation of the medicine or other fluid from the cartridge 120. In some embodiments, the drive system (not shown in FIG. 1) incrementally advances a piston rod longitudinally into the cartridge 120 so that the fluid is forced out of the output end 122 (described below). In this embodiment, the septum at the output end 122 can be pierced to permit fluid outflow when a cap member (not shown in FIG. 1, refer to cap member 315 in FIG. 5 for one example) is connected to the pump housing structure 110.

The drive system may be housed in the housing structure 110 of the pump device in a compact manner so that the pump device 100 is portable, wearable, concealable, or a combination thereof. For example, in the circumstances in which the medicine cartridge 120 has a length of about 6 cm to about 7 cm (about 6.4 cm in this embodiment), the overall length of the pump housing structure 110 (which contains medicine cartridge and the drive system) can be about 7 cm to about 9 cm (about 8.3 cm or less in this embodiment). In addition, the pump housing structure 110 may have an overall height of about 1.5 cm to about 4 cm (about 2.9 cm or less in this embodiment) and an overall thickness of about 8 mm to about 20 mm (about 14.5 mm or less in this embodiment). Accordingly, a user can conveniently wear the pump device 100 on the user's skin (e.g., skin adhesive) underneath the user's clothing or carry the pump device 100 in the user's pocket (or other portable location) while receiving the medicine dispensed from the pump device.

For example, in the circumstances in which the medicine cartridge 120 has a length of about 6 cm to about 7 cm (about 6.4 cm in this embodiment), the overall length of the pump housing structure 110 (which contains medicine cartridge and the drive system) can be about 7 cm to about 9 cm (about 8.3 cm or less in this embodiment). In addition, the pump housing structure 110 may have an overall height of about 1.5 cm to about 4 cm (about 2.9 cm or less in this embodiment) and an overall thickness of about 8 mm to about 20 mm (about 14.5 mm or less in this embodiment). In such circumstances, the controller device 200 can be figured to mate with the compact pump housing structure 110 so that, when removably attached to one another, the components define a portable infusion pump unit that stores a relatively large quantity of medicine compared to the overall size of the unit. For example, in this embodiment, the infusion pump system 10 (including the pump device 100 attached to the removable controller device 200) may have an overall length of about 7 cm to about 9 cm (about 8.5 cm or less in this embodiment), an overall height of about 1.5 cm to about 4 cm (about 3.5 cm or less in this embodiment), and an overall thickness of about 8 mm to about 20 mm (about 15 mm or less in this embodiment).

Still referring to FIG. 1, the drive system of the pump device 100 may be continuously or intermittently controlled by pump controller device 200. In this embodiment, the controller device 200 is configured to removably attach to the pump device 100, When attached, the controller device 200 communicates electronic control signals via hard-wire-connection to the drive system or other components of the pump device 100. The controller device 200 can include a controller housing structure 210 that is configured to mate with a complementary portion of the pump housing structure 110 so as to form a releasable mechanical connection. For example, the pump housing structure 110 may define a cavity 118 that mates with a complementary protruding face (not show in FIG. 1) of the controller housing structure 210 for a friction fit engagement. Also, the controller housing structure 210 may include a channel 212 that mates with a curved surface 117 of the pump housing structure 110 when the controller device 200 is attached to the pump device. In addition, one or more releasable connector devices (e.g., mating tongues and grooves, mounting protrusions friction fit into mating cavities, or the like) can be used to further implement the releasable securement of the controller device 200 to the pump device 100. Furthermore, the pump device 100 may include one or more electrical contacts 118 that are exposed to the controller device 200 and that mate with opposing electrical contacts (e.g., conductive pads, pins, and the like) on the adjacent face of the controller device 200. As such, the controller device 200 is in electrical communication with the pump device 100 and is capable of transmitting electrical signals to the pump device 100 and receiving feedback signals (e.g., sensor signals) from components within the pump device 100.

The pump controller device 200 includes a user interface 220 that permits a user to monitor the operation of the pump device 100. In this embodiment, the user interface includes a display 222 and one or more user-selectable buttons 224, 226, and 228. The display 222 may be used to communicate a number of settings or menu options for the infusion pump system 10. For example, the user may press one or more of the buttons 224, 226, and 228 to shuffle through a number of menus or program screens that show particular settings and data (e.g., review data that shows the medicine dispensing rate or the total amount of medicine dispensed in a given time period). Also, in some embodiments, the user can adjust the settings or otherwise program the controller device 200 by pressing one or more buttons 224, 226, and 228 of the user interface 220. In embodiments of the infusion pump system 10 configured to dispense insulin, the user may press one or more of the buttons 224, 226, and 228 to change the dispensation rate of insulin or to request that a bolus of insulin be dispensed. In some embodiments, the user interface 220 may include tactile buttons, a touch screen, audio inputs or outputs, or a combination thereof. Previously incorporated U.S. Provisional Application Ser. No. 60/721,267 also describes a number of configurations for a removable controller device in addition to the configuration illustrated in FIG. 1 herein.

Accordingly, when the controller device 200 is connected to the pump device 100, the user is provided with the opportunity to readily monitor infusion pump operation by simply viewing the user interface 210 connected to the pump device 100. Such monitoring capabilities may provide comfort to a user who may have urgent questions about the current operation of the pump device 100 (e.g., the user may be unable to receive immediate answers if wearing an infusion pump device having no user interface attached thereto). Also, there is no need for the user to carry and operate a separate device to monitor the operation of the infusion pump device 100, thereby simplifying the monitoring process and reducing the number of devices that must be carried by the user.

Figure 2:
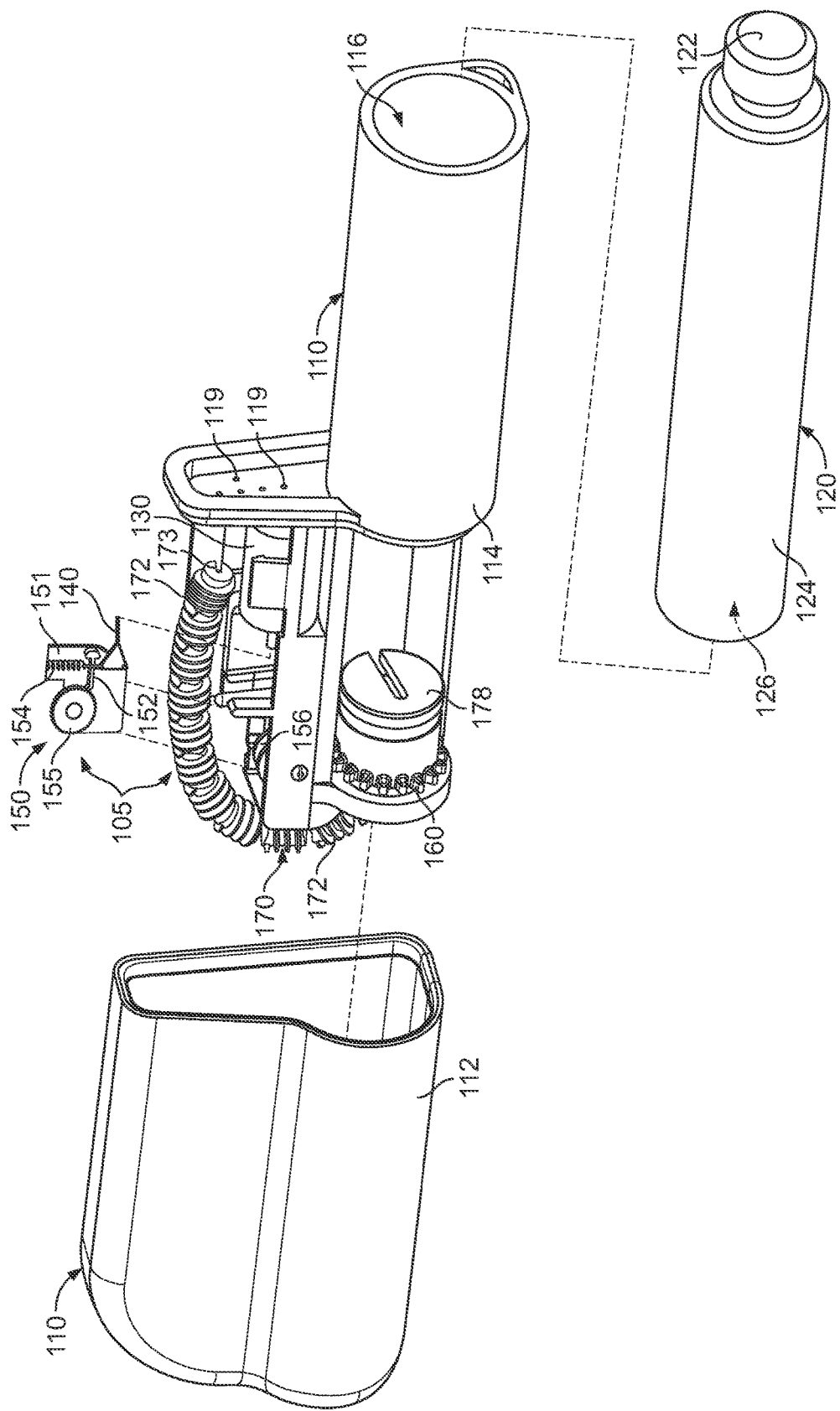
FIG. 2 is an exploded perspective of the pump device of FIG. 1.

Referring to FIG. 2, the pump device 100 includes a drive system 105 that accurately and incrementally dispenses fluid from the pump device 100 in a controlled manner. In this embodiment, the pump housing structure 110 includes a detachable shell 112 that covers at least a portion of the drive system 105 and includes a frame portion 114 to which at least a portion of the drive system 105 is mounted. The detachable shell 112 may include an inner curved surface against which a curved section of a piston rod 170 rests. The frame portion 114 define a the cavity 116 that receives the fluid cartridge 120. One or both of the detachable shell 112 and the frame portion 114 can be molded from polymer material, such as Polycarbonate, Acrylonitrile Butadiene Styrene, or Acrylic. As previously described, in some embodiments, the fluid cartridge 120 may occupy a majority of the length of the pump device 100 (with the drive system 105 being arranged in a compact manner) so that the pump device 100 is wearable and portable.

In some embodiments, the drive system 105 may include a rotational motor 130 that is coupled to a string member 140, which is used to adjust a ratchet mechanism 150. Briefly, the rotational motor 130 can be used to act upon the string member 140, thereby causing the string member 140 to adjust a pawl member 152 relative to a ratchet body 155. In this embodiment, the ratchet body 155 is in the form of a ratchet wheel. The ratchet wheel 155 can be integrally formed with, or mounted to, a worm gear 156. Incremental rotation of the ratchet wheel 155 causes rotation of a drive wheel 160 (due to engagement with the worm gear 156), which causes the incremental longitudinal advancement of a flexible piston rod 170. As the piston rod 170 is advanced into plunger chamber 126 of the fluid cartridge 120 (e.g., defined in this embodiment by the circumferential wall 124 of the fluid cartridge 120), the fluid in the cartridge 120 is forced from the septum at the output end 122. It should be understood from the description herein that, when the pump device 100 is in use, the septum at the output end 122 may be pierced by a cap member (not shown in FIG. 2) mounted to the housing structure 110, which allows fluid to exit from the cartridge 120 and enter a tube of an infusion set attached to the patient. Accordingly, the drive system 105 can provide a reliable and compact configuration for accurately dispensing the desired volume of fluid from the pump device 100. Moreover, the drive system 105 may comprise few, if any, high-cost actuator components or electronics, thereby facilitating the relatively low-cost production of a disposable and reliable pump device 100.

Referring now to the components of the drive system 105 in more detail, the rotational motor 130 may comprise a battery powered actuator having a rotatable output shaft 132. In this embodiment, the rotational motor 130 can receive signals that cause the output shaft to rotate in a first rotational direction or in a second, opposite rotational direction. One example of a suitable rotational motor 130 is a coreless DC motor supplied by Jinlong Machinery of China.

The rotational motor 130 can be mounted to the frame portion 114 of the pump housing structure 110 so that the motor 130 remains in a substantially stationary position relative to the electrical contacts 119 of the pump device 100. As such, the operation of the rotational motor 130 can be controlled by the control device 200 (FIG. 1) via electrical signals communicated through one or more of the electrical contacts 119. In some embodiments, one or more of the electrical contacts 119 may be directly connected to the inputs of the rotation motor 130, for example, to deliver control signals from a control circuit or to deliver electrical current from a battery, capacitor, or other power source disposed in the controller device 200 or disposed in the pump device 100. In other embodiments, the electrical contacts 119 may be connected to an electrical circuit (e.g., an integrated circuit implemented on a small printed circuit board) onboard the pump device 100 (e.g., mounted to the frame portion 114). In such circumstances, the control device 200 may deliver control signals via the electrical contacts 119 to the electrical circuit onboard the pump device 100, which then opens a gate or a circuit pathway to permit the electrical current to pass to the rotational motor 130 (e.g., from a battery or other power source disposed in the pump device 100).

Referring to FIGS. 2 and 3A-C, the string member 140 may be coupled to the rotational motor 130 so that actuation by the motor 130 causes the string member 140 to act upon the ratchet mechanism 150. For example, one or more full rotations of the motor 130 can be translated into a tension force in the string member 140 that is applied to a pawl member 152, which (in this embodiment) is pivotable to a reset position by the tension force from the string member 140. As such, the string member 140 is coupled between the rotational motor 130 and the ratchet mechanism 150 so as to provide a reliable and consistent adjustment of the ratchet mechanism 150. In some embodiments, the string member 140 may comprise a flexible member capable of transmitting a tension force, for example, a braided string structure (some examples are described below in connection with FIG. 3B), a monofilament string structure, a flexible tape or ribbon structure, or the like.

The string member 140 can be arranged in a loop around two or more guides (e.g., two guides 142 and 144 are shown in this embodiment). Such a loop arranged can be used to optimize the location and direction of the tension force in the string member 140 that is applied to the ratchet mechanism 150. Moreover, the loop arrangement of the string member may provide a force amplification effect when the string member 140 is wound using the rotational motor 130, which may permit the use of a smaller-sized motor in the pump design. Previously incorporated U.S. Provisional Application Ser. No. 60/720,411 also describes a number of loop arrangements for the string member 140 in addition to the illustrative example depicted in FIGS. 3A-C herein.

In the embodiment shown in FIGS. 3A-C, the string member 140 starts at the shaft 132 of the rotational motor 130, passes around a stationary guide 142, around a second guide 144 connected to the pawl member 152, and then back to the motor 130 to form a loop arrangement. The motor 130 spins such that a portion 145 the string member 140 winds upon itself, thus drawing the two guides 142 and 144 together with a force amplification effect. In some circumstances, the force amplification effect of the winding string member 140 can be approximated as:

$$F(\text{string}) = T(\text{motor})/r(\text{string}),$$

where T(motor) is the torque rating of the motor, r(string) is the radius of the string and F(string) is the subsequent pulling force on the string. To find the total force upon the guide coupled to the pawl (F(guide)):

$$F(\text{guide}) = F(\text{string}) + F(\text{String})\cos(\theta) - L(\text{friction})$$

or reducing $$F(\text{guide}) = T(\text{motor})/r(\text{string})[1+\cos(\theta)] - L(\text{friction}),$$

where cos(θ) describes the angle of the string with respect to parallel to the axis of the stationary guide and the drive guide and L(friction) represents the total losses associated with friction within the system.

As shown in FIG. 3B, the string member 140 may comprise braided filaments that are capable of enduring repeated twisting sequences of the string member 140. For example, the braided filaments may comprise one or more polymer materials, such as PET (e.g., DTex Dyneema material available from Honeywell, Inc.). Such braided filament string members are capable of enduring the torsion and frictional forces associated with undergoing thousands of cycles of twisting as described above in connection with FIGS. 2 and 3A. The string member 140 can be formed to have an outer diameter of about 0.02 mm to about 0.07 mm, and preferably about 0.05 mm. Also, in some embodiments, the string member 140 may comprise braided filaments that are arranged around a centrally disposed thin wire filament having a diameter of about 0.02 mm or less. The thin wire filament may comprise a polymer material a metallic material having a non-coarse outer surface. Such materials may also be capable of enduring the repeated twisting sequences of the string member 140. Such a construction may permit the outer filament surfaces to frictionally engage one another during the twisting process while the filament surfaces contacting the centrally disposed thin wire are exposed to a reduced friction load.

Referring again to FIG. 2, the string member 140 is coupled to the ratchet mechanism 150, which provides incremental motion to thereby advance the piston rod 170. The ratchet mechanism 150 includes the pawl member 152 and the ratchet body 155, which in this embodiment is a ratchet wheel having a number of teeth along its circumferential surface. The pawl member that is adjustable between a reset position and a forward position. For example, the rotational motor 130 may be activated to twist the string member 140 (as previously described), and the string member 140 then applies a tension force that adjusts the pawl member 152 to the reset position where the pawl member 152 engages one or more new teeth of the ratchet wheel 155. A spring device 154 is also coupled to the pawl member so as to urge the pawl member 152 toward the forward position. This spring bias causes the pawl member 152 to drive the ratchet wheel 155 an incremental amount in a forward rotational direction as the string member 140 is untwisted.

Referring again to FIGS. 3A-3C, the adjustable pawl member 152 is constructed in such a way as to engage the teeth of the ratchet wheel 155 in a single direction (e.g., in the forward rotational direction of the ratchet wheel 155). In the reverse direction, a locking pawl 159 prevents the ratchet wheel 155 from reverse motion. As such, the adjustable pawl member 152 can adjust from the forward position to the reset position (shown in FIG. 3A) to engage a new tooth of the ratchet wheel 155 while the ratchet wheel 155 remains in position due to the locking pawl 159. In this embodiment, the adjustable pawl member 152 is pivotably coupled to a support plate 151 at so that the string member 140 and the spring device 154 can act to pivot the pawl member between the reset position and the forward position. In particular, a first end portion of the pawl member 152 may be fixedly or hingedly mounted to the support plate 151 while a free end portion of the pawl member 152 engages the ratchet wheel 155. Also, in this embodiment, the locking pawl 159 is fixedly coupled to the support plate 151.

The ratchet mechanism 150 can employ a set of stopper pins 153a and 153b that limit the motion of the adjustable pawl member 152. In some embodiments, the stopper pins 153a and 153b can serve as location sensors to detect when the pawl member 152 has reached the reset position (e.g., adjacent the stopper pin 153a) or the forward position (e.g., adjacent the stopper pin 153b). For example, these sensors can be optical, magnetic, or contact type sensors. The sensors may be capable of transmitting signals that indicate when the location of the pawl member 152 is detected. Such sensor signals may be transmitted to the motor 130, to the controller device 200 (FIG. 1), or a combination thereof. Accordingly, when the pawl member 152 reaches the stopper pin 153a (e.g., by rotation of the motor 130 that causes the string member 140 to adjust the pawl member 152), a signal can indicate that the pawl member 152 has reached the limit of its travel and the motor 130 will cease rotation in that direction (e.g., end the twisting process on the string member 140 in that direction).

Referring again to FIG. 2 and FIGS. 3A-C, the driving force of the ratchet mechanism 150 can be provided by energy stored in a potential energy storage device, such as the spring device 154. Thus, when the adjustable pawl 152 is driving the ratchet wheel 155 in the forward rotational direction, the potential energy of the spring device 154 is being translated to kinetic energy for the motion of the pawl member 152 and the ratchet wheel 155. For example, in one incremental motion cycle, the pawl member 152 may start at the reset position (as shown in FIG. 3A) with the string member 140 in a twisted configuration. In response to the controller device 200 (FIG. 1) transmitting a signal to initiate the cycle, the rotational motor 130 may begin to rotate in a first rotational direction that unwinds the string member 140, thereby permitting the spring device 154 to drive the pawl member 152 toward the forward position. The rotational motor 130 continues to rotate in the first direction so that after the pawl member 152 reaches the forward position (e.g., adjacent the stopper pin 153b), the string member 140 begins to twist in the opposite orientation. Such twisting of the string member 140 causes a tension force that overcomes the bias of the spring device 154 and adjusts the pawl member 152 toward the reset position. After the pawl member 152 reaches the reset position (e.g., adjacent the stopper pin 153a), the rotational motor 130 stops rotating in the first rotational direction and the pawl member 152 remains at rest in the reset position. In the event of a second cycle, the rotational motor 130 would begin the cycle by rotating in a second rotational direction (opposite the first rotational direction) so as to unwind the string member 140 yet again. This pattern of cycles may continue until the piston rod 170 has reached the limit of its longitudinal travel (described in more detail below).

In other embodiments, the incremental motion cycle may begin with the pawl member 152 starting at the forward position (e.g., adjacent the stopper pin 153b). In such circumstances, the rotation motor 130 would rotate in a first rotational direction to twist the string until the pawl member is moved to the reset position (as shown in FIG. 3A), and then the rotational motor 130 would rotate in a second, opposite rotational direction to unwind the string member 140 until the pawl member 152 returns to the forward position.

As shown in FIG. 2, the spring device 154 can be coupled to the pawl member 152 at a first end portion and coupled to the support plate 151 at a second end portion. Alternatively, as shown in FIG. 3A, the spring device 154 can be to the pawl member 152 at a first end portion and coupled to a part of the frame portion 114 (not directly joined to the support plate 151).

Referring again to FIG. 2, in some embodiments the ratchet wheel 155 can be coupled with a worm gear 156 so that the incremental rotation of the ratchet wheel 155 is translated to the worm gear 156. Such rotation of the worm gear 156 causes a rotation of a drive wheel 160, which is rotatably mounted to the frame portion 114 of the pump device 100. The drive wheel 160 includes a central aperture having an internal thread pattern therein (not shown in FIG. 2). The internal thread pattern of the drive wheel 160 mates is an external thread pattern on the flexible piston rod 170 so that the piston rod 170 is longitudinally advanced inside the plunger chamber 126 of the fluid cartridge 120. Thus, the incremental motion of provided by the ratchet mechanism 150, the string member 140, and the motor 130 causes the drive wheel 160 to incrementally rotate, which in turn translates to a longitudinal advancement of the flexible piston rod 170. In one example, the drive system 105 can advance the piston rod 170 an increment of about 16 microns or less (about 4 microns to about 12 microns, and preferably about 7 microns to about 8 microns) for each incremental motion cycle of the motor 130, string member 140, and ratchet mechanism 150 as previously described.

In some embodiments, the flexible piston rod 170 comprises a plurality of segments 172 serially connected by hinge portions so that the flexible piston rod 170 is adjustable from a curved shape to a noncurved shape. The plurality of segments 172 and the interconnecting hinge portions can be integrally formed in one piece from a moldable material, including a number of polymer materials such as Nylon or POM. In this embodiment, the plurality of segments 172 comprise generally cylindrical segments that each include an exterior thread pattern along at least one cylindrical surface portion. A plunger connector 178 may be coupled to the leading end of the flexible piston rod 170 so as to abut against the plunger (not shown in FIG. 2) in the plunger chamber 126 of the fluid cartridge 120.

Still referring to FIG. 2, the flexible piston rod 170 can include an anti-rotation structure that hinders the piston rod 170 from rotating with drive wheel 160 (thereby allowing the rotation of the drive wheel 160 to translate into a longitudinal motion of the piston rod 170). For example, in this embodiment, the flexible piston 170 includes a longitudinal channel 173 extending through each of the segments 172. The longitudinal channel 173 can engage a complementary protrusion on the frame portion 114 (not shown in FIG. 2) proximate the drive wheel 160 so that the flexible piston rod 170 is hindered from rotating when the drive wheel 160 turns relative to the frame portion 114. Accordingly, the longitudinal channel in each segment 172 aligns to form a keyway that receives a mating key (e.g., a protrusion) on the frame portion 114. In other embodiments, the anti-rotation structure may include a plurality of longitudinal channels 173 (with each channel capable of engaging an associated protrusion that acts as a key to hinder rotation while permitting longitudinal motion), one or more flat surfaces along each segment 172 (with the flat surface slidably engaging a complementary flat surface on the frame portion 114), or the like.

In the configuration illustrated in FIG. 2, the flexible piston rod 170 is in a retracted state so that it has a generally curved shape, with some or all of the cylindrical segments 172 hinged away from the adjacent segments 172. As the rod segments 172 are advanced through the drive wheel 160, the segments 172 abut one another end-to-end so as to form a generally rigid, noncurved shape. Previously incorporated U.S. Provisional Application Ser. No. 60/720,405 also describes a number of configurations for the flexible piston rod 170 in addition to the configuration illustrated in FIG. 2 herein.

Because the flexible piston rod 170 is adjustable from a curved shape to a noncurved shape, the overall length of the pump device can be reduced in some embodiments. For example, in a typical infusion pump that houses a straight and rigid rod, the typical infusion pump requires a package or housing having a linear dimension sufficient to accommodate the length of the rigid piston rod when it is at its limit of travel in which it is fully withdrawn from the container or cylinder. This requirement for a large linear dimension can make it difficult to make the overall size of the typical infusion pump small enough for certain desired applications, such as, for example, wearable or implantable pumps. In a typical infusion pump having a rigid piston rod, the space required to house the rigid piston rod can be described by the following equation:

$$L = 2t + y, \quad (1)$$

where:
"L" is the minimum overall linear dimension or length required to support the driven member part of the device;
"t" is the required linear travel of an equivalent rigid driven member; and
"y" is an added sum for the space required to support the driving member part of the device.

It can be seen, therefore, that if the piston rod is a rigid, linear element, the relative length of unused piston rod travel can potentially double the overall length of the typical infusion pump housing.

In the embodiment depicted in FIG. 2, the space requirement of pump device 100 having the flexible piston rod 170 is substantially less than the space requirement of a similar device actuated by a rigid piston rod. This can be explained by referencing the original "space requirement" equation set forth above as Equation (1). In contrast to the space requirement of a dispensing device containing a rigid pushrod, the equation for the space required for a dispensing device containing a flexible pushrod is as follows:

$$L = t + y + z, \quad (2)$$

where:
"L" is the minimum overall linear dimension or length required to support the driven member part of the device;
"t" is the required travel of the flexible driven member (flexible pushrod);
"y" is an added sum for the space required to support the driving member; and
"z" is the space required to house the unused portion of the flexible driving member.

The space required under component "z' is a function of the properties of the flexible piston rod 170 (e.g., the curved portion of the flexible piston rod 170 before it is advanced toward the fluid cartridge 120). Thus, the pump device 100 incorporating the flexible piston rod 170 would require less space than the same device if it were to incorporate a non-flexible, rigid rod. In such circumstances, the overall length of the pump housing structure 110 can be less than twice the push rod travel length.

It should be understood that the flexible piston rod 170 may include segments that have a shape other than the generally cylindrical segments 172. For example, in an alternative to the embodiment illustrated in FIG. 2, the segments of the flexible piston rod 170 can have a generally a square or rectangular cross-section (rather than a cylindrical shape), with teeth or a thread pattern on at least one surface thereof. In these circumstances, the flexible piston rod 170 may pass through a carrier in which the drive wheel 160 is rotatably mounted. The drive wheel 160 can have a threaded edge, that engages the teeth of the rod segments. Thus, rotation of the drive wheel 160 causes a linear advancement of the flexible piston rod 170 along an axis that is parallel to the axis of rotation of the drive wheel 160, while the passage of the rod segments through the carrier aligns the segments into a linear orientation.

Figure 4:
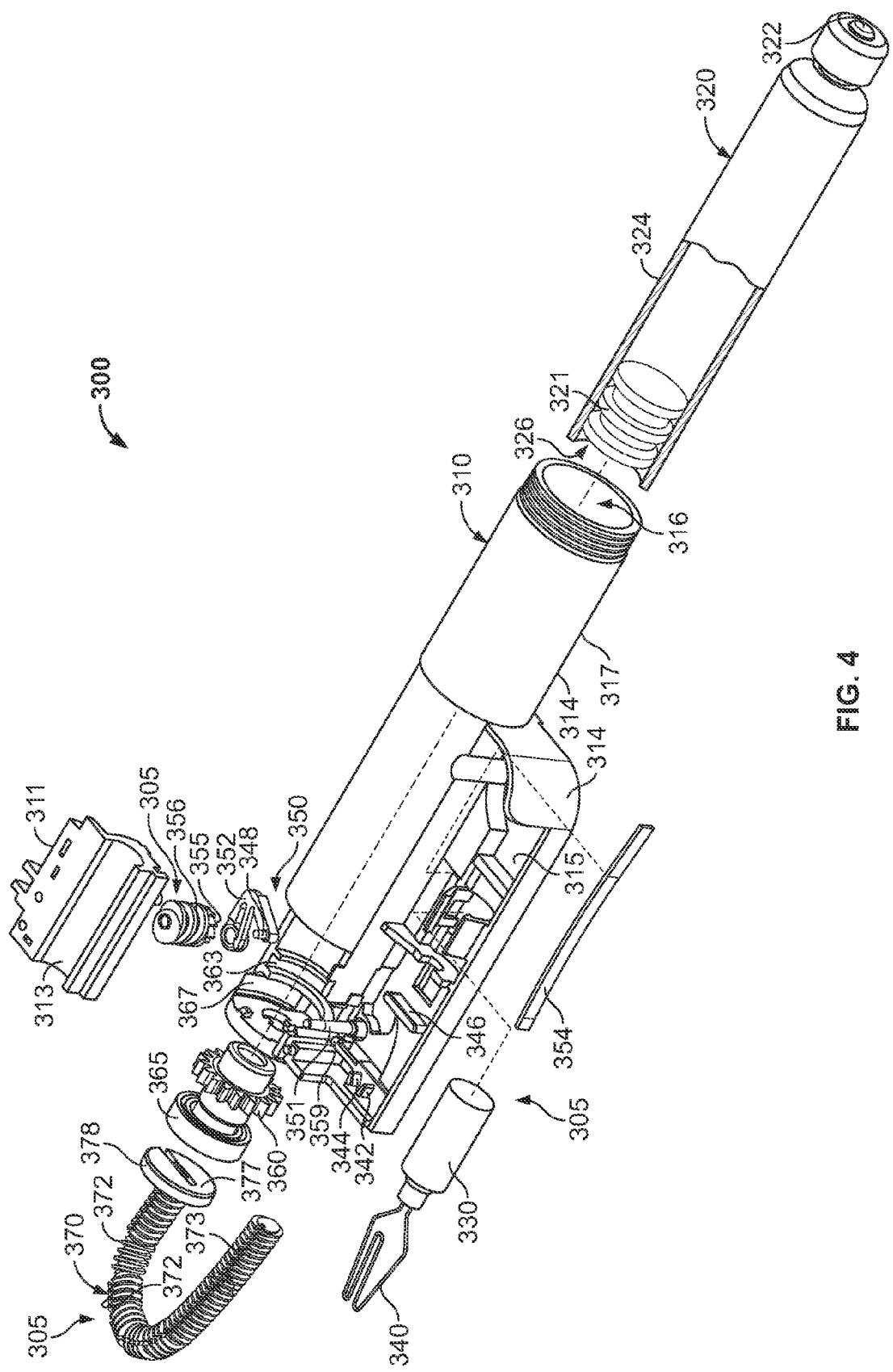
FIG. 4 is an exploded perspective view of a portion of an infusion pump device, in accordance with some embodiments.

Referring now to another embodiment of a pump device 300 as shown in FIG. 4, the drive system 305 can include a string member 340 in a loop arrangement around more than two guides, such as four guide structures 342, 344, 346, and 348. In these circumstances, the motion path of the string member 340 and the orientation of the string member 340 can be configured to provide an efficient mechanical advantage orientation during the desired motion of the adjustable pawl member 352. One of the guide structures 348 may be coupled to the adjustable pawl member 352 while the remaining guide structures 342, 344, and 346 are coupled to the frame portion 314 of the pump device 314. Accordingly, the string member 340 may have a loop configuration with more directional changes compared to the embodiments previously described in connection with FIGS. 2 and 3A.

Similar to the previously described embodiments, the pump device 300 includes a housing structure 310 that defines a cavity 316 capable of receiving a fluid cartridge 320. The housing structure 310 may include a frame portion 314 and a detachable shell portion 312 (refer to FIG. 5) so that, when assembled, the pump device 300 can have an outer configuration that mates with a removable controller device 390 (refer to FIGS. 6-7). In these embodiments, the drive system 305 can be contained in the housing structure 310 of the pump device 300 in a compact manner so that the pump device 300 is portable, wearable, concealable, or a combination thereof. Accordingly, a user can conveniently wear the pump device 300 on the user's skin (e.g., skin adhesive) underneath the user's clothing or carry the pump device 100 in the user's pocket (or another portable location) while receiving the medicine dispensed from the pump device 300.

Figure 5:
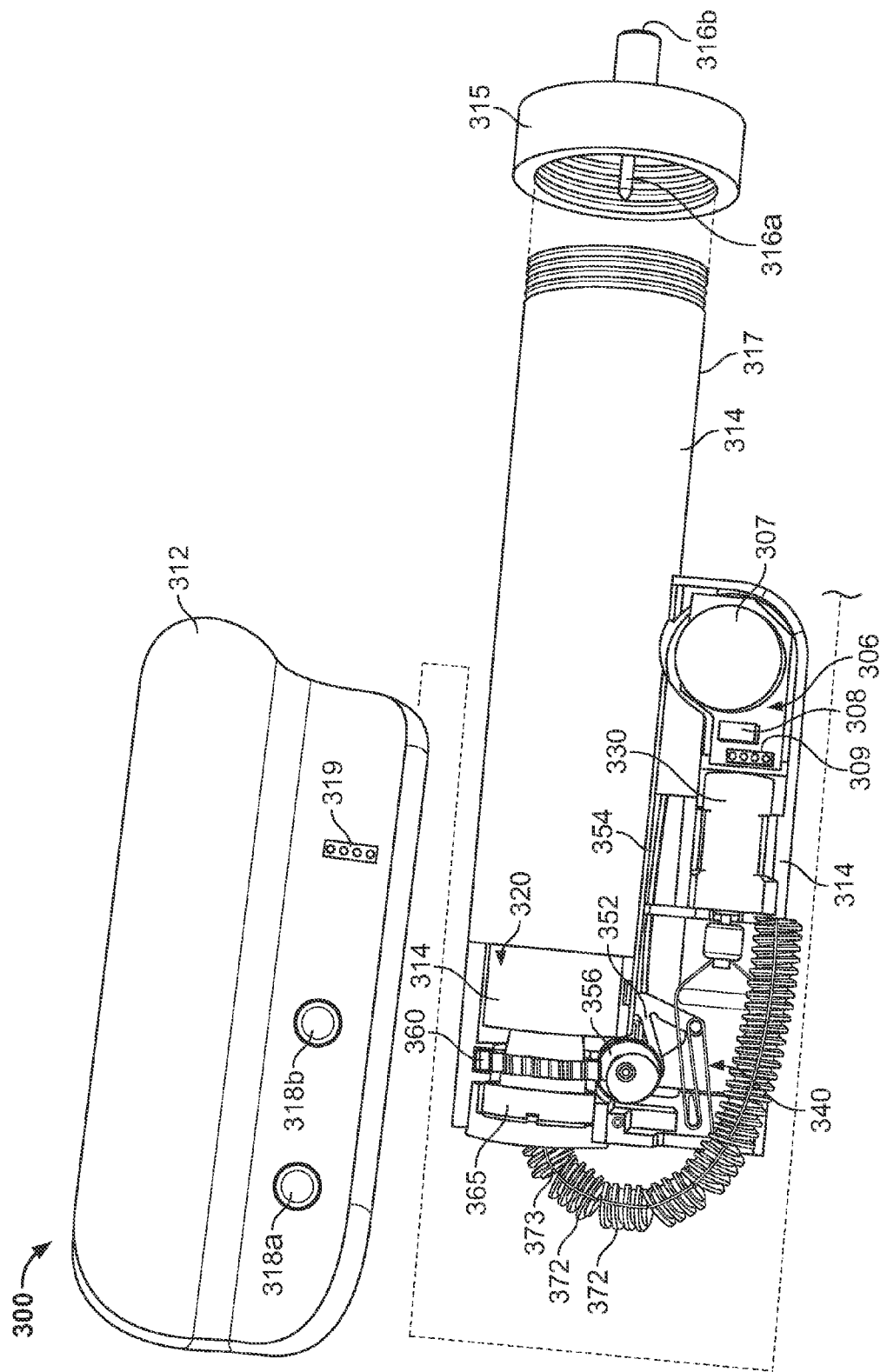
FIG. 5 is a perspective view of the portion of the infusion pump device of FIG. 4.
Figure 6:
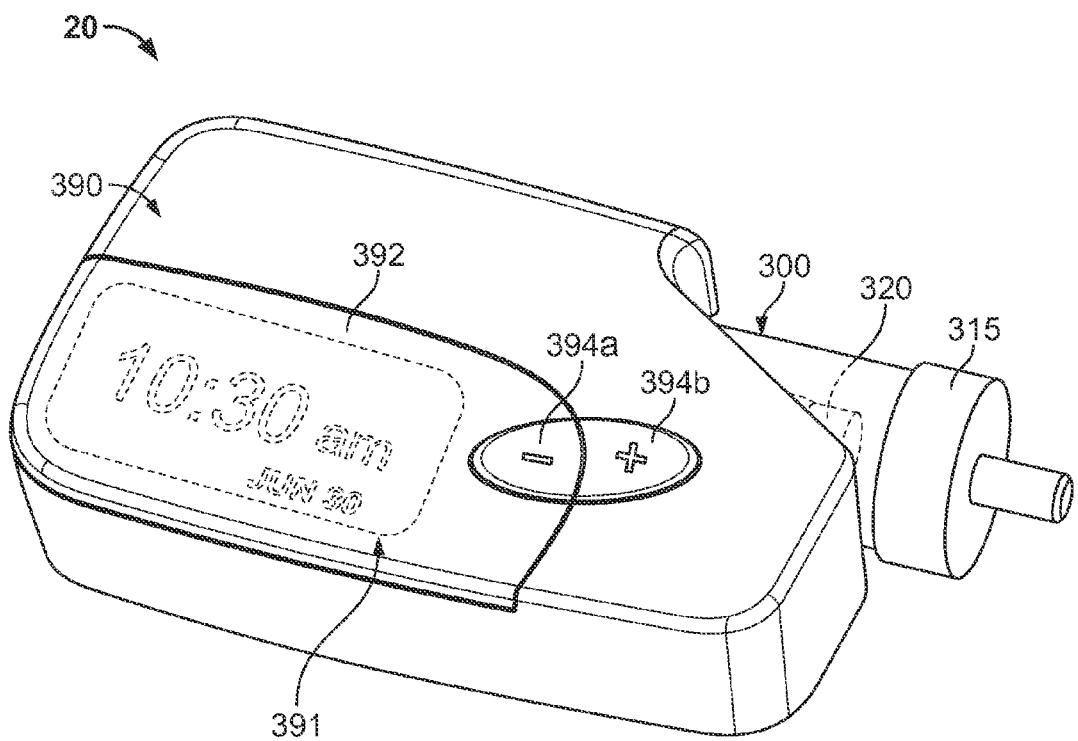
FIGS. 6-7 are perspective views of an infusion pump system including the infusion pump device of FIG. 4.
Figure 7:
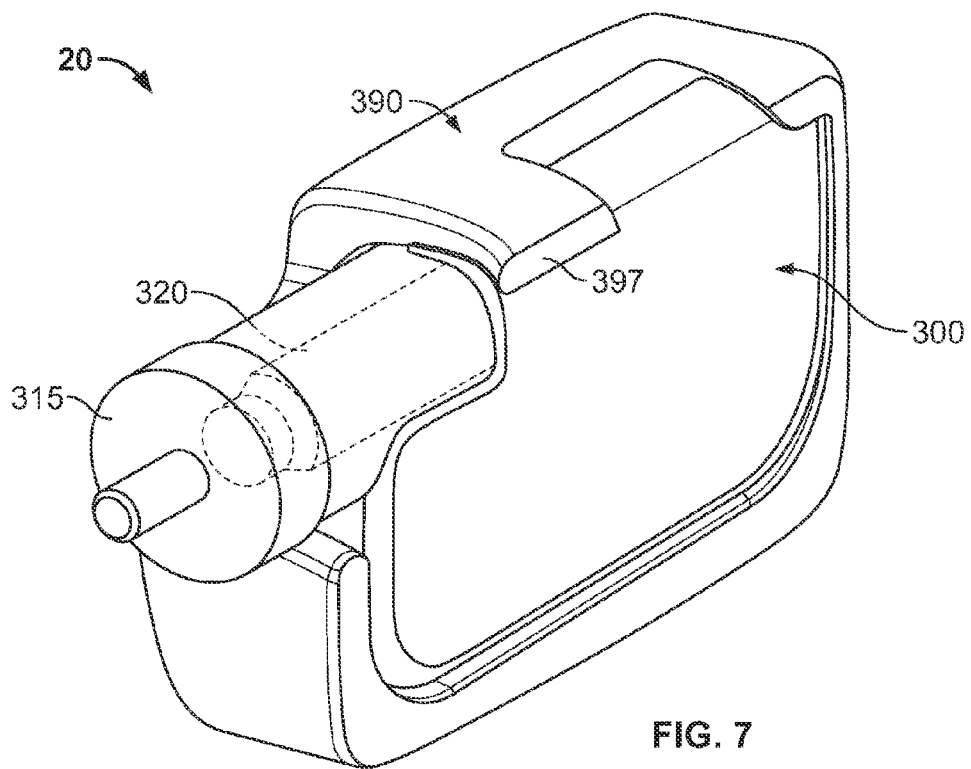

Referring to FIGS. 5-7, the pump device 300 can be part of an infusion pump system 20 in which the pump device 300 communicates with a controller device, including but not limited to the removable controller device 390 depicted in FIGS. 6-7. In this embodiment, the controller device 390 includes a user interface 391 so that the operation of the pump device 300 can be readily monitored by a user. For example, the user interface 391 may include a display 392 and two or more buttons (e.g., two buttons 394a and 394b are provided in this embodiment). The pump system 20 can be a medical infusion pump system that is configured to controllably dispense a medicine from the cartridge 320. As such, the pump device 300 can be adapted to receive a medicine cartridge 320 in the form of a preloaded carpule that contains insulin or another medicine for use in the treatment of Diabetes (e.g., Byetta®, Symlin®, or others) or other injectable medicines. Similar to previously described embodiments, the pump device 300 includes a drive system 305 that causes controlled dispensation of the medicine or other fluid from the cartridge 320. For example, the drive system 305 may incrementally advance a flexible piston rod 370 into a plunger chamber 326 of the cartridge 320 so that the fluid is force out the septum at the output end 322.

In those embodiments in which the pump device 300 is connected to a removable controller device 390, the controller device 390 can communicate control signals to the drive system 305 or other components of the pump device 300. Similar to the previously described embodiments, the controller device 390 can include a controller housing structure that is configured to mate with a complementary portion of the pump housing structure 310 so as to form a mechanical connection. For example, the controller housing structure may include a cavity that mates with a portion of the pump housing structure 310 when the controller device 390 is attached to the pump device 300. In addition, the controller device 390 may include a flexible finger 317 to mate with an complementary surface of the pump housing structure 310. Further, as shown for example in FIG. 5, the pump device 300 may include one or more magnetically attractable devices 318a and 318b that engage with complementary magnetically attractable devices of the controller device 390 (not shown in FIGS. 6-7). As such, the magnetically attractable devices 318a and 318b may contribute to releasably secure the pump device 300 to the controller device 390. Other mechanical connectors (e.g., snap-fit connectors, magnetic connectors, surface protrusions that mate with female cavities, or the like) can also be implemented to join pump housing structure 310 with the controller device.

Still referring the FIGS. 5-7, the pump device 300 may include on or more electrical contacts 319 that are exposed to the controller device 390 and that mate with opposing electrical contacts (e.g., pads, pins, or the like) on the adjacent face of the controller device 390. In this embodiment, the electrical contacts 319 are disposed on the detachable shell portion 312 of the pump housing structure 310 (refer to FIG. 5) and are aligned with an electrical contact device 309 mounted in the frame portion 314. It should be understood that, in other embodiments, the electrical contacts 319 may be arranged on the frame portion 314 rather than on the detachable shell portion 312. In this embodiment, the frame portion 314 of the pump device may define a space 315 (refer to FIG. 4) that is capable of receiving a connection circuit 306 (refer to FIG. 5). The connection circuit 306 may be simple and inexpensive so as to facilitate a low-cost pump device 300 that is disposable. The connection circuit 306 may include a battery 307 or other power source and, optionally, a gateway circuit device 308. In some circumstances, the gateway circuit device 308 may be under the control of and directed by the control circuit in the controller device 390. The connection circuit 306 provides the electrical contact device 309 so as to facilitate electrical communication with the removable controller device 390. As such, the controller device 390 capable of transmitting electrical signals to the pump device 300 and is capable of receiving feedback signals (e.g., sensor signals) from the components in the pump device 300. For example, the gateway circuit device 308 of the circuit 309 may be in electrical communication (e.g., via one or more electrical wires or electrically conductive traces) with a force sensor 377 (refer to FIG. 8) arranged between the plunger connector 378 that the plunger 321. The force sensor 377 may comprise a force transducer or load cell that is capable of electrically communicating an applied force. As such, the force sensor 377 can provide feedback signals to the circuit 309 (or to the control device 390 via the electrical contacts) so as to monitor the force transmitted to the plunger 321 of the medicine cartridge 320. Such information can be used, for example, to detect if an occlusion exists in the medicine flow path. Other sensors (e.g., a pressure sensor, a flow sensor, a rotation sensor, a displacement sensor, or the like) may be electrically connected to the circuit 306 to provide feedback signals to the circuit 306 (or to the control device 390 via the electrical contacts). It should be understood that, in other embodiments, the connection circuit 306 may be configured to operate without the gateway circuit device 308. For example, the control circuit in the removable controller device 390 may communicate via the electrical contacts directly with a portion of the drive system 305 (e.g., direct electrical communication with the motor 330), with one or more sensors disposed in the pump device 300, and with the battery 307.

Figure 8:
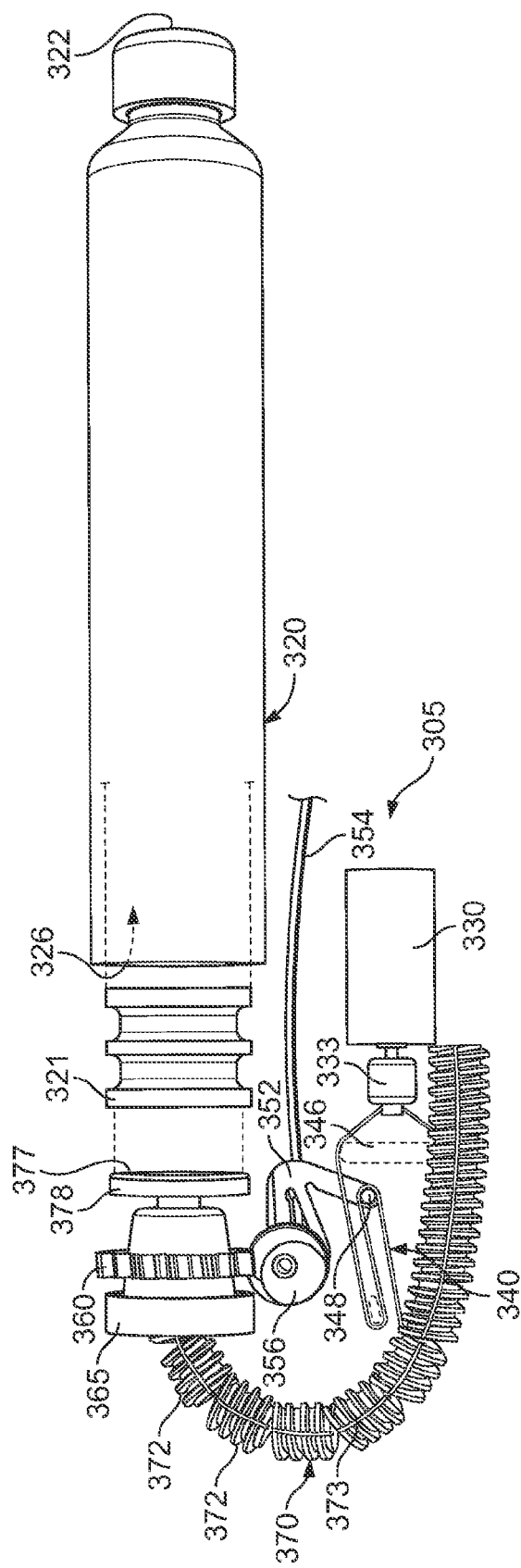
FIG. 8 is a perspective view of a drive system of the infusion pump device of FIG. 4.

Referring to FIGS. 4-5 and 8, the pump device 300 includes a drive system 305 that is capable of accurately and incrementally dispensing fluid from the fluid cartridge 320 in a controlled manner. Similar to the previously described embodiments, the drive system 305 may include the rotational motor 330 that is coupled to the string member 340. Briefly, the rotational motor 330 can be used to act upon the string member 340, thereby causing the string member 340 to adjust a pawl member 352 relative to a ratchet body 355. In this embodiment, the ratchet body 355 is in the form of a ratchet wheel that is integrally formed with a worm gear 356. Incremental rotation of the ratchet wheel 355 causes rotation of a drive wheel 360, which causes the incremental longitudinal advancement of a flexible piston rod 370. As the piston rod 370 is advanced into plunger chamber 326 (e.g., defined in this embodiment by the circumferential wall 324 of the fluid cartridge 320), the fluid in the cartridge 320 is forced from septum at the output end 322. As shown in FIG. 5, when the pump device 300 is in use, the septum at the output end 322 may be pierced by a cap member 315 mounted to the housing structure 310, which can provide fluid communication from the cartridge 320 to an infusion set tube attached to the patient. For example, the cap member 315 may include a penetrator device 316a that provides fluid communication from the medicine cartridge 320 to a tube connection end 316b. Accordingly, the drive system 305 can provide a reliable and compact configuration for accurately dispensing the desired volume of fluid from the pump device 300. Moreover, the drive system 305 may comprise few, if any, high-cost actuator components or electronics, thereby facilitating the production of a disposable and reliable pump device 300. (It should be understood that FIG. 5 depicts the drive system 305 mounted to the frame portion 314 of the pump device 300, and FIG. 8 shows a similar view with the frame portion 314 removed for purposes of illustrating the drive system 305 and the fluid cartridge 320.)

As shown in FIG. 4, some components of the drive system 305 can be retained by the frame portion 314, a cover mount 311 that is assembled to the frame portion 314, or a combination thereof. For example, the rotational motor 330, the string member 340, and the spring device 354 can be assembled into the frame portion 314 and then retained by the cover mount 311. The adjustable pawl member 352, the ratchet wheel 355, and the worm gear 356 can be assembled onto and axle 351 that is integrally formed with the frame portion 314 and then retained by the cover mount 311. A locking pawl 359 can be integrally formed with the frame portion 314 so as to align with the ratchet wheel 355 when the ratchet wheel 355 is assembled onto the axle 351. Also, the drive wheel 360 and an adjacent bearing 365 (to facilitate rotation of the drive wheel 360 relative to the frame portion 314) can be received in annular channels 363 and 367, respectively, of the frame portion 314. When the cover mount 311 is assembled to the frame portion 314, the cover mount 311 can restrict the radial or axial movement of the drive wheel 360 while permitting forward rotation of the drive wheel 360. In another example, the "unused" or retracted portion of the piston rod 370 may rest in a channel 313 defined in the top of the cover mount 311. In such a construction, the cover mount 311 and the frame portion 314 can collectively permit the desired motion of the components of the drive system 305 while reducing the likelihood of "backlash" movement or component dislodgement (which might otherwise occur, for example, when the pump device 300 is dropped to the ground).

Figure 9:
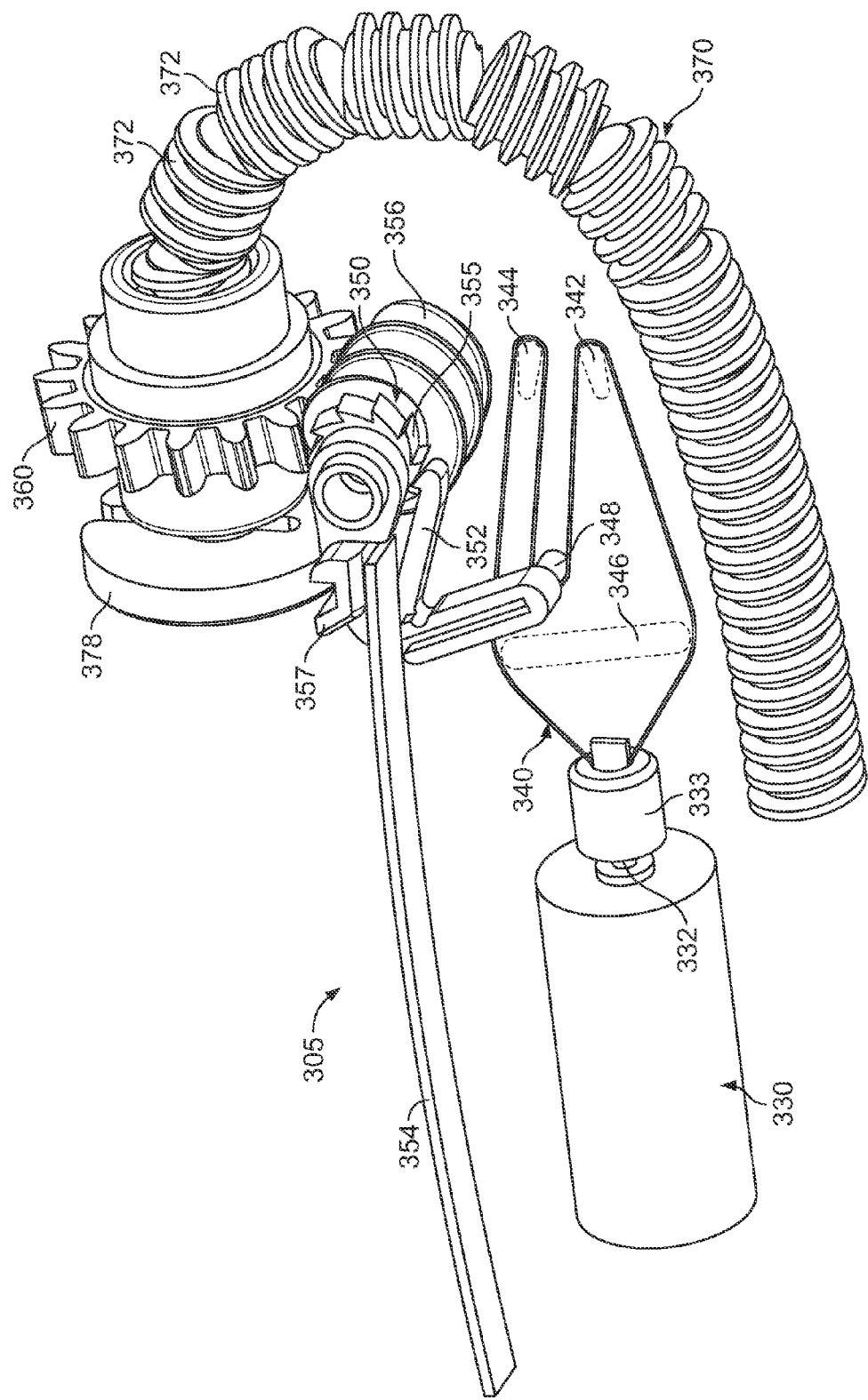
FIG. 9 is a perspective view of the drive system of FIG. 4 in a first position.
Figure 10:
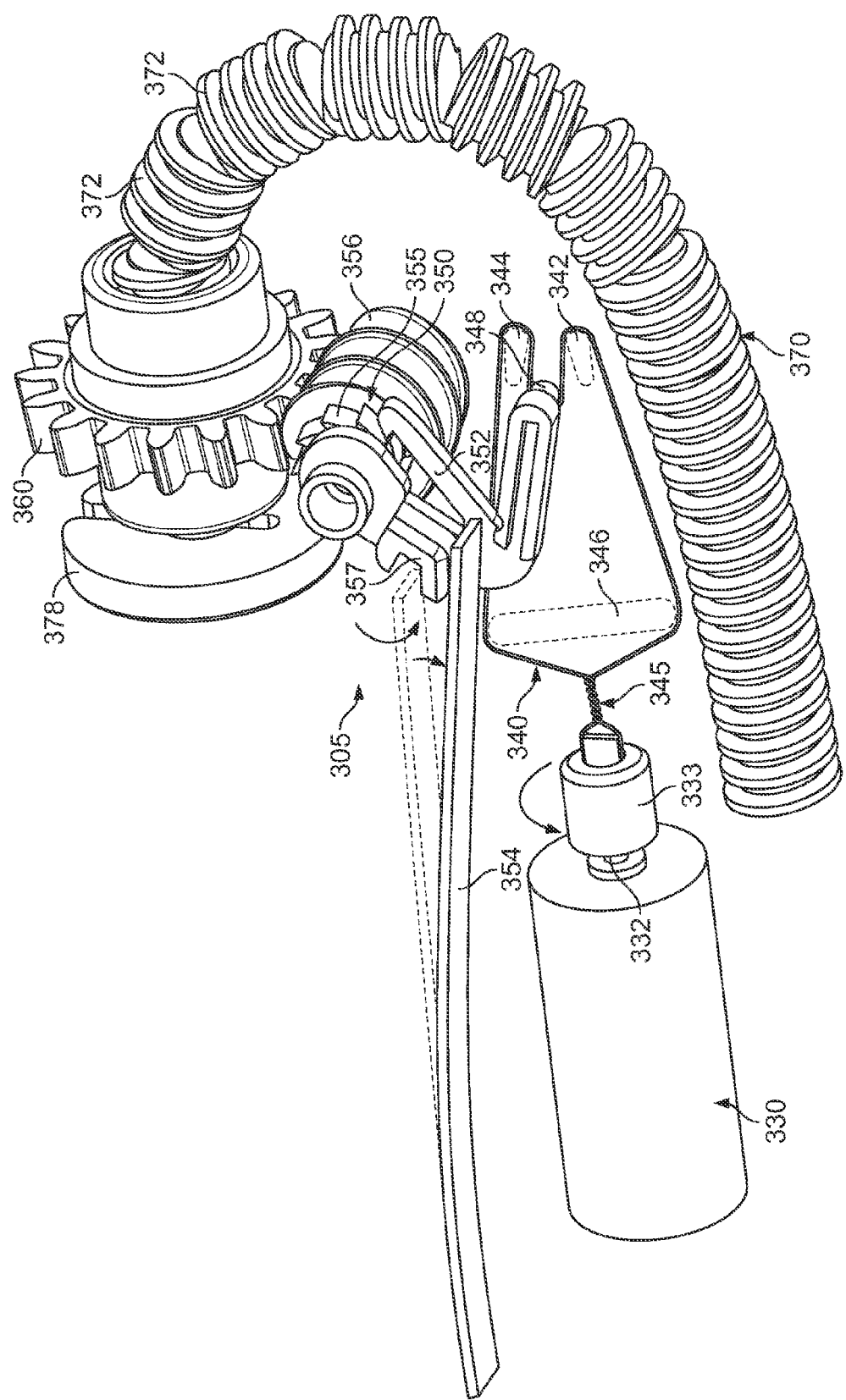
FIG. 10 is a perspective view of the drive system of FIG. 4 in a second position.

Referring now in more detail to the components of the drive system 305 depicted in FIGS. 9-10, the rotational motor 330 may comprise an electrically power actuator having a rotatable output shaft 332. In this embodiment, the rotational motor 330 can receive signals that cause the output shaft to rotate in a first rotational direction or in a second, opposite rotational direction. As previously described, one example of a suitable rotational motor 330 is a coreless DC motor supplied by Jinlong Machinery of China. Also as previously described, the operation of the rotational motor 330 can be controlled by a control device (e.g., removable control device 200 as described in connection with FIG. 1 or the like) via electrical signals communicated through one or more electrical contacts.

Still referring to FIGS. 9-10, the string member 340 may be coupled to the rotational motor 330 so that actuation by the motor 330 causes the string member to act upon the ratchet mechanism 350. One or more full rotations of the motor 330 can be translated into a tension force in the string member 340 that is applied to a pawl member 352, which (in this embodiment) is pivoted to a reset position by the tension force from the string member 140. As such, the string member 340 is coupled between the rotational motor 330 and the ratchet mechanism 350 so as to provide a reliable and consistent adjustment of the ratchet mechanism 350. In this embodiment, the string member 340 is coupled to the motor shaft 332 using a mechanical connector 333. Similar to previously described embodiments, the string member 140 may comprise a flexible member capable of transmitting a tension force, for example, a braided string structure, a monofilament string structure, a flexible tape or ribbon structure, or the like.

The string member 340 can be arranged in a loop around two or more guide structures (e.g., four guide structures 342, 344, 346, and 348 are shown in this embodiment). The motion path of the string member 340 and the orientation of the string member 340 can be configured to provide an efficient mechanical advantage orientation during the desired motion of the adjustable pawl member 352. In this embodiment, one of the guide structures 348 is coupled to the adjustable pawl member 352 while the remaining guide structures 342, 344, and 346 are integrally formed with the frame portion 314 of the pump device 300 (guide structures 342, 344, and 346 are shown in dotted lines to represent their location on the frame portion 314 (not shown in FIGS. 9-10)). Also, the guide structure 346 exemplifies how a single guide structure can have two sliding surfaces that oppose one another, thereby functioning similar to a configuration having two different guides. As described in connection with previous embodiments, the loop arrangement of the string member 340 may provide a force amplification effect when the string member 340 is wound using the rotational motor 330.

In the embodiment shown in FIGS. 9-10, the string member 340 starts at the shaft 332 of the rotational motor 330, passes around a first sliding surface of the guide structure 346, around a second guide structure 342, around a third guide structure 348 connected to the adjustable pawl member 352, around a fourth guide structure 344, around a second sliding surface of the guide structure 346, and then back to the motor 330 to form the loop arrangement. As shown in FIG. 10, when the motor 330 rotates, a portion 345 the string member 340 twists upon itself, thus drawing the guide structure 348 toward the stationary guide structures 342 and 344. The orientation of the stationary guide structures 342 and 344 relative to the guide structure 348 (connected to the pawl member 352) can be configured to provide an efficient mechanical advantage for the tension force applied by the string member 340 during the desired motion of the adjustable pawl member 352.

The string member 340 is coupled to the ratchet mechanism 350, which provides incremental motion to thereby advance the piston rod 370. The ratchet mechanism 350 includes the pawl member 352 and the ratchet body 355, which in this embodiment is a ratchet wheel having a number of teeth along its circumferential surface. The pawl member 352 is adjustable between a reset position (refer to FIG. 10) and a forward position (refer to FIG. 9). For example, the rotational motor 330 may be activated to twist the string member 340, and the string member 340 then applies a tension force that adjusts the pawl member 352 to the reset position in which the pawl member 352 grabs a new tooth of the ratchet wheel 335 (refer to FIG. 10). In this embodiment, the adjustable pawl member 352 is pivotably coupled to about the axis of the axle 351 (refer to FIG. 4) that receives the ratchet wheel 355 and the worm gear 356.

A spring device 354 is also coupled to the pawl member 352 so as to urge the pawl member 352 toward the forward position (refer to FIG. 9). In this embodiment, the spring device 354 is in the form of a leaf spring that is fixed to the frame portion 314 (refer to FIG. 4) at a first end portion and that is engaged with an abutment protrusion 357 of the pawl member 352 at a second end portion. Thus, as shown in FIG. 10, when the pawl member 352 is adjusted to the reset position, the spring device 354 is flexed and stores potential energy that urges the pawl member 152 to return to the forward position (refer to FIG. 9) and thereby drive the ratchet wheel 355 in a forward rotational direction. As previously described, a locking pawl 359 coupled to the frame portion 314 (refer to FIG. 4) prevents the ratchet wheel 355 from reverse motion. As such, the adjustable pawl member 352 can adjust from the forward position (refer to FIG. 9) to the reset position (refer to FIG. 10) to engage a new tooth of the ratchet wheel 355 while the ratchet wheel 355 remains in position due to the locking pawl 359.

It should be understood that the drive system 305 can employ a set of stopper pins (similar to previously described embodiments) that limit the motion of the adjustable pawl member 352 or that serve as location sensors to indicate when the pawl member 352 has reach the reset position or the forward position. For example, these sensors can be optical, magnetic, or contact type sensors. The sensors may be capable of transmitting signals that indicate when the location of the guide structure 348 or the pawl member 352 is detected. Such sensor signals may be transmitted to the motor 330, to the controller device, or a combination thereof.

Still referring to FIGS. 9-10, in some embodiments the ratchet wheel 355 can be integrally formed with the worm gear 356 so that the incremental rotation of the ratchet wheel 355 is translated to the worm gear 356. Such rotation of the worm gear 356 causes a rotation of a drive wheel 360, which is rotatably mounted to the frame portion 314 of the pump device 300. Similar to previously described embodiments, the drive wheel 360 includes a central aperture having an internal thread pattern therein (not shown in FIGS. 9-10), which mates is an external thread pattern on the flexible piston rod 370. Thus, the incremental motion provided by the ratchet mechanism 350, the string member 340, and the motor 330 causes the drive wheel 360 to incrementally rotate, which in turn translates to a linear advancement of the flexible piston rod 370.

Accordingly, in some embodiments, the piston rod 370 may undergo only forward or positive displacement as a result of drive system 305. For example, the drive system 305 substantially hinders the piston rod 370 from retracting or "backing up" in response to fluid pressure in the medicine cartridge 320 or other reversal forces. In such circumstances, the flexible piston rod 370 can be retracted only upon disassembly of the pump device 300 (e.g., to disengage the gears or the ratchet mechanism). In those embodiments in which the pump device 300 is intended to be disposable, the non-retractable piston rod configuration (due to the drive system 305) may facilitate a "one time use" disposable pump device, thereby reducing the likelihood of failure due to non-intended repeated use of the disposable pump device.

The flexible piston rod 370 comprises a plurality of segments 372 serially connected by hinge portions so that the flexible piston rod 370 is adjustable from a curved shape to a noncurved shape. As previously described, the plurality of segments 372 and the interconnecting hinge portions can be integrally formed in one piece from a moldable material, including one or more polymer materials such as Nylon or POM. In this embodiment, the plurality of segments 372 comprise generally cylindrical segments that each include an exterior thread pattern along at least one cylindrical surface portion. A plunger connector 378 may be coupled to the leading end of the flexible piston rod 370 so as to abut against or connect with the plunger 321 in the plunger chamber 326 of the fluid cartridge 320. Previously incorporated U.S. Provisional Application Ser. No. 60/720,405 also describes a number of configurations for the flexible piston rod 370 in addition to the configuration illustrated in FIGS. 9-10 herein.

Figure 11A:
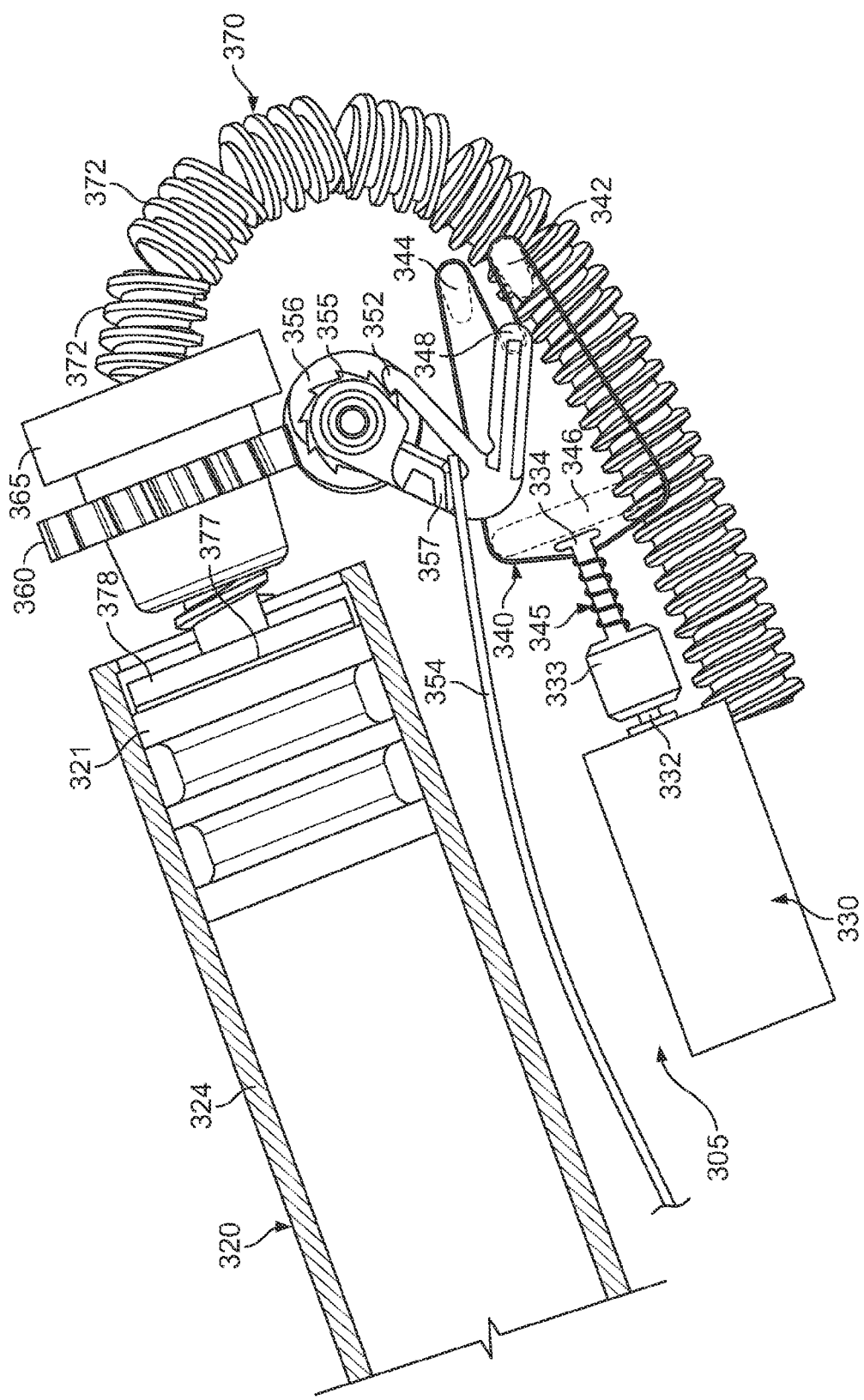
FIGS. 11A-C are perspective views of a portion of the infusion pump device of FIG. 4.
Figure 11B:
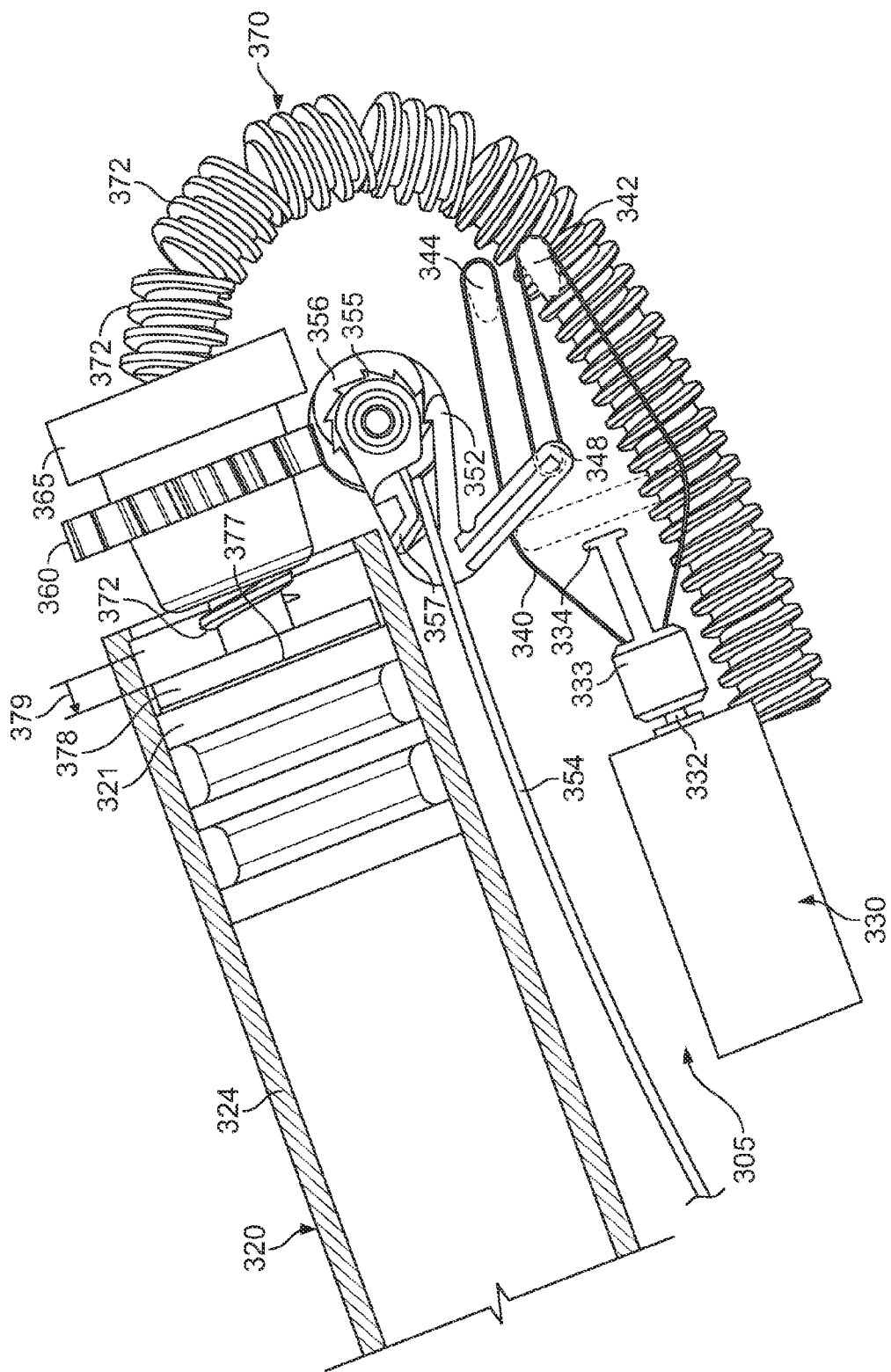
Figure 11C:
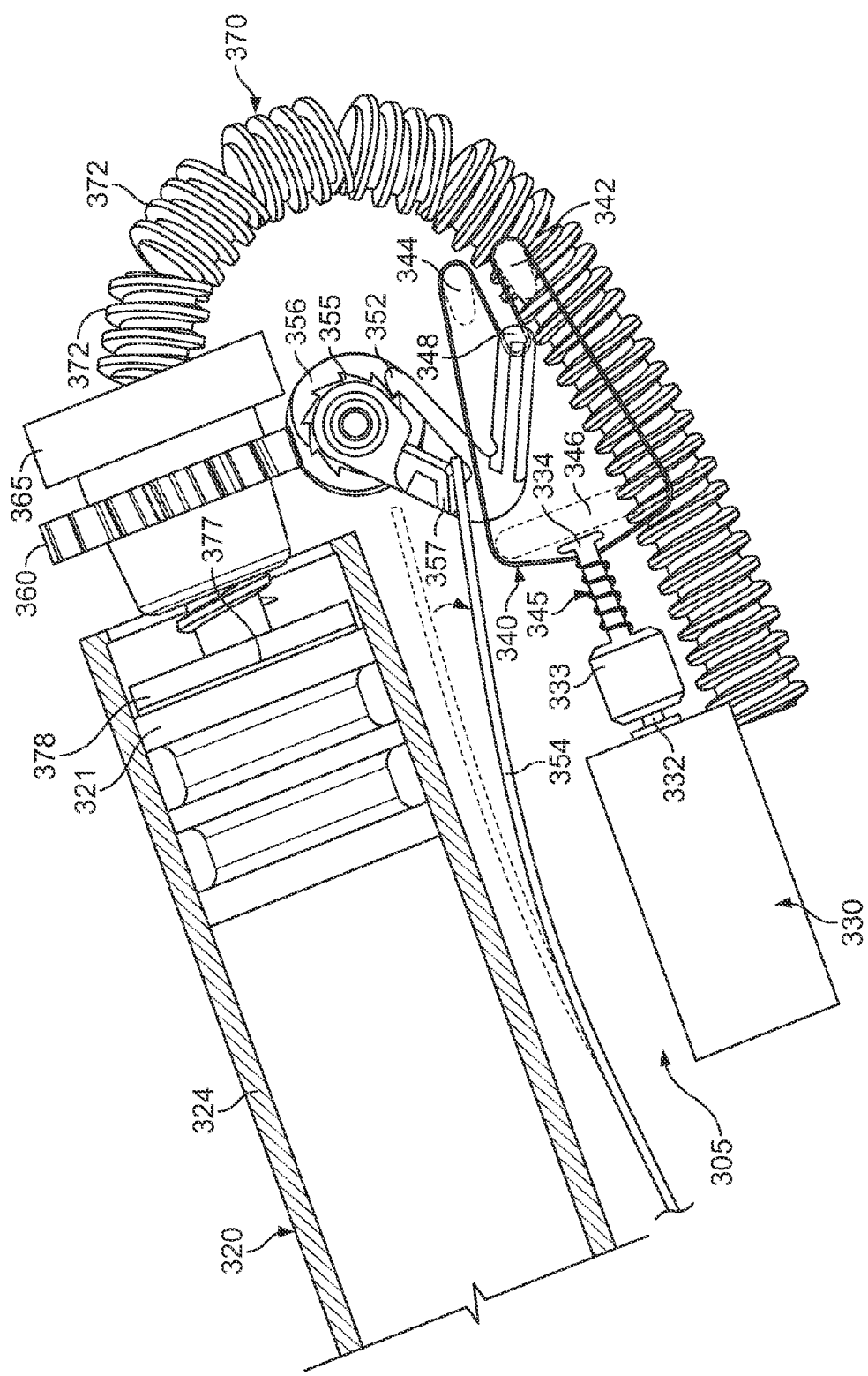

Referring now to FIGS. 11A-C, the incremental motion cycle of the drive system 305 may include rotation of the motor 330 so that the string member 340 transitions from a twisted state, to an untwisted state, and then again to a twisted state. Such a transition of the string member 340 can cause the pawl member 352 to adjust from the reset position (refer to FIG. 11A), to the forward position (refer to FIG. 11B), and back to the reset position (refer to FIG. 11C). The adjustment of the pawl member 352 from the reset position to the forward position drives the ratchet wheel 355 and worm gear 356, which incrementally rotates the drive wheel 360 and thereby advances the flexible piston rod 370 a longitudinal increment distance 379 (refer to FIG. 11B). In one example, the drive system 305 can advance the piston rod 370 a longitudinal increment distance 379 of about 16 microns or less (about 4 microns to about 12 microns, and preferably about 7 microns to about 8 microns) for each incremental motion cycle of the motor 330, string member 340, and ratchet mechanism 350 as previously described herein.

As shown in FIGS. 11A-C, some embodiments of the motor 330 may include a mandrel 334 extending axially from the mechanical connector 333 or the motor shaft 332. The mandrel can be arranged so that the string member 340 is configured to twist around the mandrel 334 in response to rotation by the motor shaft 332. The frictional wear upon the string material may be reduced because the string member engages and twists around the mandrel 334 rather than engaging an opposing string material surface and twisting upon itself.

Referring to now FIG. 11A, in this embodiment of the incremental motion cycle, the pawl member 352 begins at the reset position with the string member 340 in a twisted configuration at string portion 345. As previously described, the string portion 345 is twisted around the mandrel 334 that extends axially from the motor 330. When the adjustable pawl member 352 is in the reset position as shown in FIG. 11A, it is capable of engaging a tooth of the ratchet wheel 355.

Referring to FIG. 11B, in response to the controller device transmitting a signal to initiate the cycle, the rotational motor 330 may begin to rotate in a first rotational direction that unwinds the string member 340, thereby permitting the spring device 354 to drive the pawl member 352 toward the forward position (refer to FIG. 11B). When the adjustable pawl 352 is driving the ratchet wheel 355 in the forward rotational direction, the potential energy of the spring device 354 is being translated to kinetic energy for the motion of the pawl member 352 and the ratchet wheel 355. Such an adjustment of the pawl member 352 from the reset position to the forward position drives the ratchet wheel 355 and the integrally formed worm gear 356. The incremental rotation of the worm gear 356 results in an incremental rotation by the drive wheel 360, which advances the flexible piston rod 370 the longitudinal increment distance 379. Such an incremental advancement of the flexible piston rod 370 may cause a predetermined volume of fluid to be dispensed from the cartridge 320 (FIG. 4).

Referring to FIG. 11C, the rotational motor 330 continues to rotate in the first rotational direction so that after the pawl member 352 reaches the forward position, the string member 340 begins to twist in the opposite orientation. As previously described, the string member 340 is twisted around the mandrel 334 that extends axially from the motor 330. Such twisting of the string member 340 causes a tension force that overcomes the bias of the spring device 354 and adjusts the pawl member 352 toward the reset position. When the adjustable pawl member 352 reaches the reset position, as shown in FIG. 11C, the pawl member is capable of engaging a new tooth of the ratchet wheel 355. The locking pawl 359 (shown in FIG. 4) prevents the ratchet wheel 355 from rotating in a reverse (non-forward) rotational direction while the adjustable pawl member 352 is shifting back to the reset position. Such an adjustment of the pawl member 352 back to the reset position causes the spring device 354 to flex (as shown in FIG. 11C), thereby storing potential energy to drive the adjustable pawl member 352 and ratchet wheel 355 in a subsequent cycle. After the pawl member 352 reaches the reset position, the rotational motor 330 stops rotating in the first rotational direction and the pawl member 352 remains at rest in the reset position (refer to FIG. 11C). In the event of a subsequent cycle, the rotational motor 330 would begin the cycle by rotating in a second rotational direction (opposite the first rotational direction) so as to unwind the string member 340 yet again. This pattern of cycles may continue until the piston rod 370 has reached the limit of its longitudinal travel.

It should be understood, that in other embodiments, the incremental motion cycle may begin with the pawl member 352 starting at the forward position (refer to FIG. 11B). In such circumstances, the rotation motor 330 would rotate in a first rotational direction to twist the string until the pawl member is moved to the reset position (refer to FIG. 11C), and then the rotational motor 330 would rotate in a second, opposite rotational direction to unwind the string member 340 until the pawl member 352 returns to the forward position (refer again to FIG. 11B).

Similar to the previously described embodiments, the string member 340 may comprise braided filaments that are capable of enduring repeated twisting sequences of the string member 340. The braided filaments may comprise a polymer such as PET. Such braided filament string members are capable of enduring the torsion and frictional forces associated with undergoing thousands of cycles of twisting as described above in connection with FIGS. 11A-C. The string member 340 can be formed to have an outer diameter of about 0.02 mm to about 0.07 mm, and preferably about 0.05 mm. Also, in some embodiments, the string member 340 may comprise braided filaments that are arranged around a centrally disposed thin wire filament (e.g., comprising a polymer material or a metallic material) having a diameter of about 0.02 mm or less, which is also capable of enduring the repeated twisting sequences of the string member 340. Such a construction may permit the outer filament surfaces to frictionally engage one another during the twisting process while the filament surfaces contacting the centrally disposed thin wire are exposed to a reduced friction load.

Figure 12:
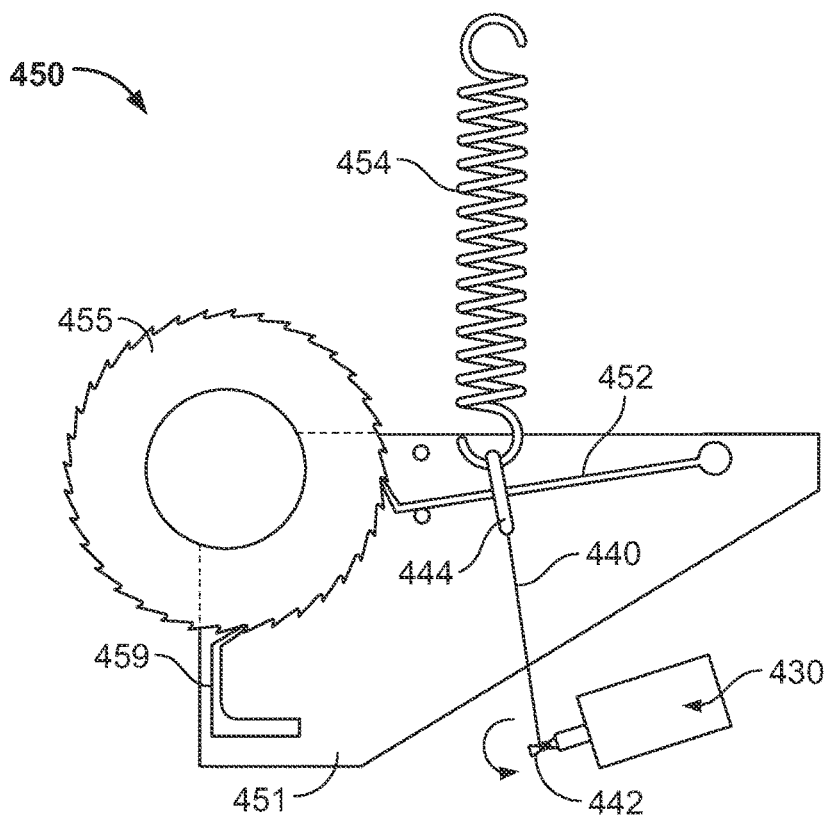
FIG. 12 is a diagram of a portion of an infusion pump device, in accordance with some embodiments.
Figure 13:
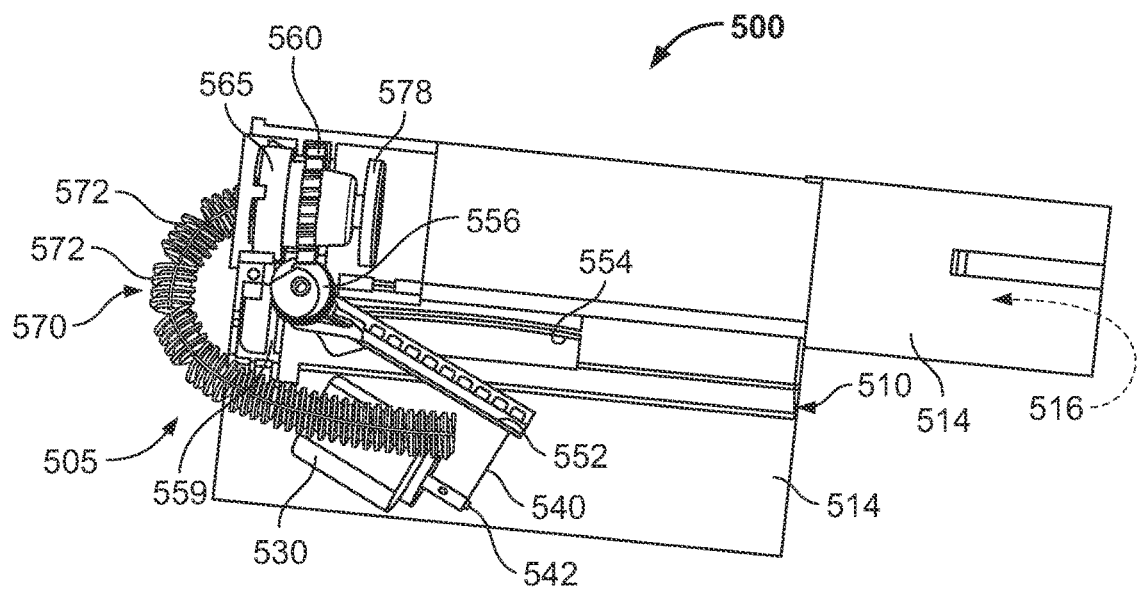
FIG. 13 is a perspective view of a portion of the infusion pump device, in accordance with some embodiments.
Figure 14:
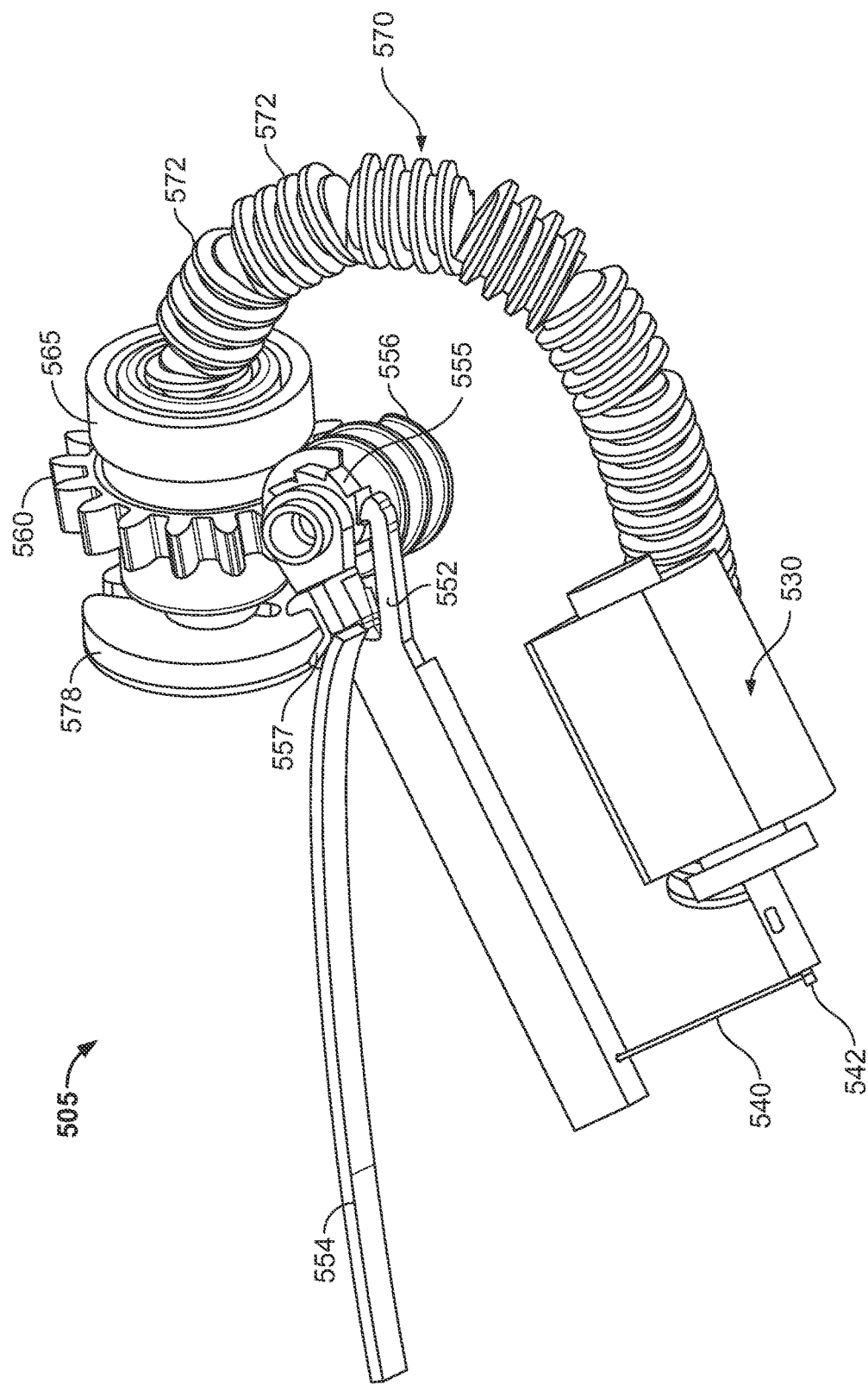
FIG. 14 is a perspective view of a drive system of the infusion pump device of FIG. 13.

Referring now to FIGS. 12-14, some embodiments of a pump device 400 can include a string member and a rotational motor like the previously described embodiments, except that the string member 440 is configured to wind (or unwind or both) around a spindle device. Such a configuration may reduce the torsion and friction loads upon the string member material while providing a tension force to adjust the ratchet mechanism. Moreover, the spindle configuration may further reduce the space requirements for drive system in the pump housing, thereby providing a reliable and compact infusion pump system that is portable and wearable by the user.

Referring to FIG. 12, a ratchet mechanism 450 that is configured to assemble within a pump device (similar to the ratchet mechanism 150 in pump device 100 described in connection with FIG. 3A) is adjusted by a string member 440 that can wind around a spindle device 442. The ratchet mechanism 450, string member 440, spindle device 442, and motor 430 can be part of a drive system for the pump device (similar to the drive system 105 of the pump device 100 described in connection with FIG. 2) that provides a reliable and consistent configuration for accurately dispensing the desired volume of fluid from the infusion pump device. Also, similar to the previously described embodiments, the drive system including the string member 440, the motor 430, and the spindle device 442 may comprise few, if any, high-cost components, thereby facilitating the production of a disposable infusion pump device. Because the pump device may house the drive system in a compact manner, the pump device can be portable, wearable, and readily concealable by the user.

As shown in FIG. 12, the spindle device 442 can be coupled to a rotational motor 430 so that the spindle device 442 rotates with the motor shaft. A string member 440 can be attached to the spindle device 442 so that the string member 440 winds or unwinds around the spindle device 442 in response to the rotation of the motor 430. Similar to previously described embodiments, the string member 440 may comprise a flexible member capable of transmitting a tension force, for example, a braided filament structure, a monofilament string structure, a flexible tape or ribbon structure, or the like. For example, in some embodiments, the string member 440 may comprise a flexible tape material having generally flat opposing surfaces, thereby permitting the tape material to be wrapped around itself when being wound on the spindle device 442.

The string member 440 is also coupled to the ratchet mechanism 450, which provides incremental motion to thereby advance the piston rod (not shown in FIG. 12). The ratchet mechanism 450 includes the pawl member 452 and the ratchet body 455, which in this embodiment is a ratchet wheel having a number of teeth along its circumferential surface. The pawl member 452 is adjustable between a reset position (refer to FIG. 12) and a forward position. For example, the rotational motor 430 may be activated to rotate the spindle device 442 and thereby wind the string member 440 (as previously described), and the string member 440 then applies a tension force that adjusts the pawl member 452 to the reset position. In the reset position, the pawl member 452 can engage one or more new teeth of the ratchet wheel 455. A spring device 454 is also coupled to the pawl member 452 so as to urge the pawl member 452 toward the forward position. This spring force causes the pawl member 452 to drive the ratchet wheel 455 an incremental amount in a forward rotational direction. Similar to the embodiments previously described in connection with FIG. 3A, a locking pawl 459 prevents the ratchet wheel 455 from reverse motion. As such, the adjustable pawl member 452 can adjust from the forward position to the reset position (shown in FIG. 12) to engage a new tooth of the ratchet wheel 455 while the ratchet wheel 455 remains in position due to the locking pawl 459.

In this embodiment, the ratchet mechanism 450 can employ a set of stopper pins (as previously described) that limit the motion of the adjustable pawl member 452. In some embodiments, the stopper pins can serve as location sensors to detect when the pawl member has reach the reset position or the forward position. For example, these sensors can be optical, magnetic, or contact type sensors.

Accordingly, in one incremental motion cycle, the pawl member 452 may start at the reset position (as shown in FIG. 12) with the string member 440 wound around the spindle device 442. In response to the controller device (not shown in FIG. 12) transmitting a signal to initiate the cycle, the rotational motor 430 may begin to rotate in a first rotational direction that unwinds the string member 440 from the spindle device 442, thereby permitting the spring device 454 to force the pawl member 452 toward the forward position.

The rotational motor 430 continues to rotate in the first rotational direction so that after the pawl member 452 reaches the forward position, the string member 440 begins to wind around the spindle device 442 in the opposite orientation. Such winding of the string member 440 causes a tension force that overcomes the bias of the spring device 454 and adjusts the pawl member 452 toward the reset position. After the pawl member reaches the reset position, the rotational motor 430 stops rotating in the first rotational direction and the pawl member 452 remains at rest in the reset position. In the event of a second cycle, the rotational motor 430 would begin the cycle by rotating in a second rotational direction (opposite the first rotational direction) so as to unwind the string member 440 from the spindle device 442 yet again.

In other embodiments, the incremental motion cycle may begin with the pawl member 452 starting at the forward position. In such circumstances, the rotational motor 430 would rotate in a first rotational direction to wind the string member 440 around the spindle device until the pawl member 452 is moved to the reset position (as shown in FIG. 12), and then the rotational motor 430 would rotate in a second, opposite rotational direction to unwind the string member 440 from the spindle device 442 until the pawl member 452 returns to the forward position.

Referring now to another embodiment of a pump device 500 as shown in FIGS. 13-14, the drive system 505 can include a string member 540 that is configured to wrapped around a spindle device 542. In these circumstances, the orientation of the string member 540 can be configured to provide an efficient mechanical advantage during the desired motion of the adjustable pawl member 552. Moreover, such a configuration may reduce the torsion and friction loads upon the string member material and may further reduce the space requirements for drive system 505 of the pump device 500. Similar to previously described embodiments, the string member 540 may comprise a flexible member capable of transmitting a tension force, for example, a braided filament structure, a monofilament string structure, a flexible tape or ribbon structure, or the like. For example, in some embodiments, the string member 540 may comprise a flexible tape material having generally flat opposing surfaces, thereby permitting the tape material to be wrapped around itself when being wound on the spindle device 542.

Similar to the previously described embodiments, the pump device 500 includes a housing structure 510 that defines a cavity 516 capable of receiving a fluid cartridge (not shown in FIGS. 13-14). The housing structure 510 may include a frame portion 514 and a detachable shell portion (removed from FIGS. 13-14 for purposes of illustration) so that, when assembled, the pump device 500 can have an outer appearance similar to that of pump device 300 depicted in FIG. 5. In these embodiments, the drive system 505 can be contained in the housing structure 510 of the pump device 500 in a compact manner so that the pump device 500 is portable, wearable, concealable, or a combination thereof. Similar to previously described embodiments, the pump device 500 can be part of an infusion pump system in which the pump device communicates with a controller device, including but not limited to the removable controller device 390 described in connection with FIGS. 5-7. The controller device can communicate control signals to the drive system 505 or other components of the pump device 500. For example, the pump device 500 may include on or more electrical contacts that are exposed to the controller device and that mate with opposing electrical contacts (e.g., pads, pins, or the like) on the adjacent end of the controller device. In this embodiment, the pump system is a medical infusion pump system that is configured to controllably dispense a medicine. As such, the pump device 500 can be adapted to receive a medicine cartridge in the form of carpule that contains insulin or another medicament for use in the treatment of Diabetes (e.g., exenatide, Byetta™, or others), or other injectable medicines.

Still referring to FIGS. 13-14, the pump device 500 includes a drive system 505 that is capable of accurately and incrementally dispensing fluid from the fluid cartridge in a controlled manner. Similar to the previously described embodiments, the drive system 505 may include a rotational motor 530 that is coupled to a string member 540. Briefly, the rotational motor 530 can be used to wind (or unwind or both) the string member 540 around a spindle device 542, which causes the string member 540 to adjust a pawl member 552 relative to a ratchet body 555. In this embodiment, the ratchet body 555 is in the form of a ratchet wheel that is integrally formed with a worm gear 556. Incremental rotation of the ratchet wheel 555 causes rotation of a drive wheel 560, which causes the incremental linear advancement of a flexible piston rod 570. As the piston rod 570 is advanced in the forward longitudinal direction, fluid dispenses from the pump device 500. Accordingly, the drive system 505 can provide a reliable and compact configuration for accurately dispensing the desired volume of fluid from the pump device 500. Moreover, the drive system 505 may comprise few, if any, high-cost actuator components or electronics, thereby facilitating the production of a disposable and reliable pump device 500.

Referring to FIG. 14 (note that the frame portion 514 has been removed from FIG. 14 for purposes of illustration), the string member 540 is coupled to the ratchet mechanism, which provides incremental motion to thereby advance the piston rod 570. The ratchet mechanism includes the pawl member 552 and the ratchet body 555, which in this embodiment is a ratchet wheel having a number of teeth along its circumferential surface. The pawl member 552 is adjustable between a reset position and a forward position (refer to FIG. 14). For example, the rotational motor 530 may be activated to wind the string member 540 around the spindle device 542, and the string member 540 then applies a tension force that adjusts the pawl member 552 to the reset position in which the pawl member 552 grabs a new tooth of the ratchet wheel 555. A spring device 554 is also coupled to the pawl member 552 so as to urge the pawl member 552 toward the forward position. In this embodiment, the spring device 554 is a leaf spring that is fixed to the frame portion 514 (refer to FIG. 13) at a first end portion and that is engaged with an abutment protrusion 557 of the pawl member 552 at a second end portion. Thus, when the pawl member 552 is adjusted to the reset position, the spring device 554 is increasingly flexed and thereby stores potential energy that urges the pawl member 552 to return to the forward position. Similar to previously described embodiments, a locking pawl coupled to the frame portion 514 (refer to FIG. 13) prevents the ratchet wheel 555 from reverse motion. As such, the adjustable pawl member 552 can adjust from the forward position to the reset position to engage a new tooth of the ratchet wheel 555 while the ratchet wheel 555 remains in position due to the locking pawl 559.

In this embodiment, the ratchet wheel 555 is integrally formed with the worm gear 556 so that the incremental rotation of the ratchet wheel 555 is translated to the worm gear 556. Such rotation of the worm gear 556 causes a rotation of a drive wheel 560, which is rotatably mounted to the frame portion 514 using a bearing 565. Similar to previously described embodiments, the drive wheel 560 includes a central aperture having an internal thread pattern therein (not shown in FIGS. 13-14), which mates with an external thread pattern on the flexible piston rod 570. Thus, the incremental motion provided by the ratchet mechanism 550, the string member 540, and the motor 530 causes the drive wheel 560 to incrementally rotate, which in turn translates to a linear advancement of the flexible piston rod 570. A plunger connector 578 may be coupled to the leading end of the flexible piston rod 570 so as to abut against or connect with the plunger in the fluid cartridge.

Still referring to FIG. 14, the incremental motion cycle of the drive system 505 may include rotation of the motor 530 so that the string member 540 transitions from a wrapped state (e.g., wound around the spindle device 542), to an unwrapped state, and then to a wrapped state. Such a transition of the string member 540 can cause the adjustable pawl member 552 to transition from the reset position, to the forward position (refer to FIG. 14), and back to the reset position. As previously described, the adjustment of the pawl member 552 from the reset position to the forward position drives the incremental rotation of the drive wheel 560, which advances the flexible piston rod 570 a longitudinal increment distance. In one example, the drive system 505 can advance the piston rod 570 a longitudinal increment distance of about 16 microns or less (about 4 microns to about 12 microns, and preferably about 7 microns to about 8 microns) for each incremental motion cycle of the motor 530, string member 540, and ratchet mechanism 550 as previously described herein. It should be understood, that in other embodiments, the incremental motion cycle may begin with the pawl member 552 starting at the forward position (refer to FIG. 14). In such circumstances, the rotation motor 530 would rotate in a first rotational direction to wind the string member 540 around the spindle device 542 until the pawl member 552 is moved to the reset position, and then the rotational motor 530 would rotate in a second, opposite rotational direction to unwind the string member 540 until the pawl member 552 returns to the forward position.

A number of embodiments of the invention have been described. Nevertheless, it will be understood that various modifications may be made without departing from the spirit and scope of the invention. Accordingly, other embodiments are within the scope of the following claims.

What is claimed is:

1. A portable and wearable infusion pump system, comprising:
   a portable housing defining a space to receive a medicine;
   a pump drive system positioned within the portable housing so as to dispense medicine from the portable housing when the medicine is received in the space; and
   control circuitry that electrically communicates with the pump drive system via an electrical connection with the pump drive system to control dispensation of the medicine from the portable housing when the medicine is received in the space, the control circuitry being in communication with a user interface that is configured to receive user input related to dispensing the medicine and that is configured to display information related to dispensing the medicine,
   wherein pump drive system positioned within the portable housing comprises: a battery-powered motor to rotate one or more full rotations in response to one or more electrical signals communicated from the control circuitry via the electrical connection; a piston rod movable to dispense a portion of the medicine from the portable housing; and a mechanism to advance the piston rod toward the medicine housed in the portable housing, the mechanism comprising a pawl, a coupling member, a spring, and a ratchet wheel, the pawl comprising a pivotable body attached to and extending from a pivot point, the coupling member being connected between the pivotable body and the battery-powered motor, the pawl positioned to engage one or more teeth of the ratchet wheel, wherein the pawl is adjustable between a reset position and a forward position to move the ratchet member in a forward direction so as to cause the piston rod to advance toward the medicine, wherein the spring provides a bias to the pawl that urges the pawl to pivot about the pivot point towards the forward position to incrementally advance the ratchet wheel, wherein the one or more full rotations of the battery-powered motor causes the coupling member to move the pivotable body of the pawl to overcome the bias of the spring and pivot toward the reset position.

2. The pump system of claim 1, wherein the control circuitry activates the battery-powered motor to rotate one or more full rotations in a first rotational direction and one or more full rotations in a second rotational direction when the pawl is adjusted toward said one of the reset position or the forward position.

3. The pump system of claim 1, wherein the piston rod of the pump drive system comprises a threaded piston rod that is advanced in a longitudinal direction by an incremental distance in response to movement of the ratchet wheel in the forward direction.

4. The pump system of claim 3, wherein the piston rod of the pump drive system comprises a flexible piston rod having a plurality of threaded rod segments that are hingedly connected in series, the flexible piston rod being adjustable from a curved configuration to a generally straight configuration within the portable housing.

5. The pump system of claim 1, wherein the control circuitry is housed in a controller housing that is removably attachable to the portable housing.

6. The pump system of claim 5, wherein one or more external electrical contacts disposed on the controller housing are engageable with corresponding external electrical contacts disposed on the portable housing when the controller housing is removably attached to the portable housing.

7. A portable and wearable infusion pump system, comprising:
   a portable housing defining a space to receive a medicine;
   a pump drive system positioned within the portable housing so as to dispense medicine from the portable housing when the medicine is received in the space; and
   control circuitry that electrically communicates with the pump drive system via an electrical connection with the pump drive system to control dispensation of the medicine from the portable housing when the medicine is received in the space, the control circuitry being electrically connected to a user interface that is configured to receive user input related to dispensing the medicine and that is configured to display information related to dispensing the medicine,
   wherein the pump drive system positioned within the portable housing comprises: a battery-powered motor to rotate one or more full rotations in response to one or more electrical signals communicated from the control circuitry via the electrical connection; a piston rod movable to dispense a portion of the medicine from the portable housing; and a mechanism to advance the piston rod toward the medicine housed in the portable housing, the mechanism comprising a pawl and a ratchet member, the pawl positioned to engage one or more teeth of the ratchet member, wherein the pawl is adjustable between a first position and a second position to move the ratchet member in a forward direction so as to cause the piston rod to advance toward the medicine, wherein the one or more full rotations of the battery-powered motor cause the pawl to adjust toward one of the first position or the second position, wherein the pump drive system comprises a string member coupled to an output of the battery-powered motor and coupled to the pawl; and wherein the pump drive system further comprises a spindle coupled to the string member and the battery-powered motor so that the one or more rotations of the motor causes the string member to wind or unwind around the spindle to thereby adjust the pawl relative to the ratchet body.

8. The pump system of claim 7, wherein the string member is twisted by the one or more rotations of the output of the motor and thereby urges the pawl toward the reset position.

9. The pump system of claim 7, wherein the one or more rotations by the output of the motor causes the string member to apply a tension force to the pawl.

* * * * *